US008299030B2

(12) United States Patent
Cuthbertson et al.

(10) Patent No.: US 8,299,030 B2
(45) Date of Patent: *Oct. 30, 2012

(54) PEPTIDE-BASED COMPOUNDS

(75) Inventors: Alan Cuthbertson, Oslo (NO); Bard Indrevoll, Oslo (NO); Magne Solbakken, Oslo (NO); Torgrim Engell, Oslo (NO); Colin Mill Archer, Amersham (GB); Harry John Wadsworth, Amersham (GB)

(73) Assignee: GE Healthcare Limited, Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/204,935

(22) Filed: Aug. 8, 2011

(65) Prior Publication Data

US 2012/0020882 A1    Jan. 26, 2012

Related U.S. Application Data

(60) Continuation of application No. 12/423,953, filed on Apr. 15, 2009, now Pat. No. 7,994,134, which is a division of application No. 10/753,729, filed on Jan. 8, 2004, now Pat. No. 7,521,419, which is a continuation of application No. PCT/NO02/00250, filed on Jul. 8, 2002.

(30) Foreign Application Priority Data

Jul. 10, 2001    (GB) .................................. 0116815.2
Oct. 11, 2001    (NO) .................................. 20014954

(51) Int. Cl.
*A61K 38/00*    (2006.01)
*A61K 38/12*    (2006.01)
*C07K 14/705*    (2006.01)

(52) U.S. Cl. ..................................... 514/19.1; 514/21.1
(58) Field of Classification Search .......................... None
See application file for complete search history.

(56) References Cited

U.S. PATENT DOCUMENTS

| | | | |
|---|---|---|---|
| 4,647,447 A | 3/1987 | Gries et al. | |
| 5,364,613 A | 11/1994 | Sieving et al. | |
| 5,367,080 A | 11/1994 | Toner et al. | |
| 5,846,782 A | 12/1998 | Wickham et al. | |
| 5,888,474 A | 3/1999 | Dean et al. | |
| 5,965,107 A | 10/1999 | Dean et al. | |
| 7,351,790 B2* | 4/2008 | Cuthbertson et al. | 530/317 |
| 7,410,943 B2* | 8/2008 | Cuthbertson et al. | 514/1.1 |
| 7,521,419 B2* | 4/2009 | Cuthbertson et al. | 514/1.1 |
| 7,608,243 B2* | 10/2009 | Cuthbertson et al. | 424/1.69 |
| 7,737,252 B2* | 6/2010 | Cuthbertson | 530/317 |
| 7,811,551 B2* | 10/2010 | Cuthbertson et al. | 424/9.4 |
| 7,875,701 B2* | 1/2011 | Solbakken et al. | 530/329 |
| 7,897,142 B2* | 3/2011 | Cuthbertson et al. | 424/9.6 |
| 7,994,134 B2* | 8/2011 | Cuthbertson et al. | 514/19.1 |
| 2003/0176639 A1 | 9/2003 | Cuthbertson et al. | |
| 2003/0204049 A1 | 10/2003 | Cuthbertson et al. | |
| 2005/0070466 A1* | 3/2005 | Cuthbertson et al. | 514/10 |
| 2006/0193773 A1* | 8/2006 | Cuthbertson et al. | 424/1.69 |
| 2007/0183977 A1* | 8/2007 | Cuthbertson et al. | 424/9.6 |
| 2008/0095701 A1* | 4/2008 | Solbakken et al. | 424/1.89 |
| 2008/0095704 A1* | 4/2008 | Cuthbertson et al. | 424/9.1 |
| 2008/0187493 A1* | 8/2008 | Cuthbertson et al. | 424/9.2 |
| 2008/0267881 A1* | 10/2008 | Cuthbertson et al. | 424/9.4 |
| 2009/0203584 A1* | 8/2009 | Cuthbertson et al. | 514/10 |
| 2009/0232741 A1* | 9/2009 | Cuthbertson et al. | 424/9.6 |
| 2009/0263320 A1* | 10/2009 | Cuthbertson | 424/1.69 |
| 2010/0256330 A1* | 10/2010 | Cuthbertson | 530/317 |
| 2011/0117016 A1* | 5/2011 | Solbakken et al. | 424/1.73 |

FOREIGN PATENT DOCUMENTS

| | | |
|---|---|---|
| EP | 578083 | 1/1994 |
| WO | WO 89/00557 | 1/1989 |
| WO | WO 90/14103 | 11/1990 |
| WO | WO93/12819 | 7/1993 |
| WO | WO 95/14714 | 6/1995 |
| WO | WO 95/25543 | 9/1995 |
| WO | WO 95/26205 | 10/1995 |
| WO | WO 96/11023 | 4/1996 |
| WO | WO 97/06791 | 2/1997 |
| WO | WO 97/10507 | 3/1997 |
| WO | WO 97/25073 | 7/1997 |
| WO | WO 97/28830 | 8/1997 |
| WO | WO 98/10795 | 3/1998 |
| WO | WO 98/47541 | 10/1998 |
| WO | WO 98/54346 | 12/1998 |
| WO | WO 98/54347 | 12/1998 |
| WO | WO 99/39734 | 8/1999 |
| WO | WO 99/40214 | 8/1999 |
| WO | WO 99.51638 | 10/1999 |
| WO | WO 01/77145 | 10/2001 |
| WO | WO 02/20610 | 3/2002 |
| WO | WO 02/26776 | 4/2002 |
| WO | WO2004/080492 | 9/2004 |

OTHER PUBLICATIONS

Ruoslahti, J. Clin. Invest., 87: 1-5 (1991).
Conforti, G., et al. (1992) Blood 80: 37-446.
Pasqualini, R., et al. (1997) Nature Biotechnology 15: 542-546.
Bauer, J.S., (1992) J. Cell Biol. 116: 477-487.
Gehlsen, K.R., (1988) J. Cell biol. 106: 925-930.
Haubner et al. In the J. Nucl. Med. (1999).
Merrifield: J. Am. Chem. Soc., 85: 2149 (1964).
International Preliminary Examination Report dated Jan. 9, 2004 for PCT/NO02/00250.
Hallahan, D. "Targeting drug delivery to radiation-induced neoantigens in tumor microvasculature" Journal of Controlled Release 74 (2001) pp. 183-191.
Harris, T. "Tc-99m-labeled fibrinogen receptor antagonists: design and synthesis of cyclic RGD peptides for the detection of thrombi" Bioorganic & Medicinal Chemistry Letters vol. 6, No. 15, pp. 1741-1746, 1996.

(Continued)

*Primary Examiner* — Marcela M Cordero Garcia

(57) ABSTRACT

The invention relates to new peptide-based compounds for use as diagnostic imaging agents or as therapeutic agents wherein the agents comprise targeting vectors which bind to integrin receptors.

20 Claims, No Drawings

OTHER PUBLICATIONS

Liu, et.al. "99mTc-labeling of a hydrazinonicotinamide-conjugated vitronectin receptor antagonists useful for imaging tumors" bioconjugate Chem. 2001, 12, pp. 623-629.

Merrifield "Solid phase peptide synthesis" Contribution for the Rockfeller Institute, published Jan. 31, 1963, pp. 2149-2154.

Pearson, et.al. Thrombus imaging using technetium-99-m-labeled high potency GPIIb/IIIa receptor antagonists. J. Med. Chem 1996, 39, pp. 1372-1382.

Rajopadhye, et.al. Synthesis and technetium-99m labelling of cyclic GP IIB/IIa receptor antagonist conjugated to 4, 5-bis(mercaptoacetamido)-Pentanoic Acid (MAPT): Biorganic & Medicinal Chemistry Letters, 1996, vol. 6, No. 15, pp. 1737-1740.

Rajopadhye, et.al. "Synthesis evaluation and Tc-99m complexation of a hydrazinonicotinyl conjugate of hydrazinonicotinyl conjugate of a GPII/IIa antagonist cyclic peptide for the detection of deep vein thrombosis" Bioorganic & Medicinal Chemistry letters, 1997, vol. 7, No. 8, pp. 955-960.

Sivolapenko, et.al. "Imaging of metastic melanoma utilising a technetium-99m labelled RGD-containing synthetic peptide" European Journal of Nucelar Medicine 1998, vol. 25, No. 10, pp. 1383-1389.

Uehara, et.al. "The integrity of the disulfide bond in a cyclic somatostatin analog during 99mTc complexation reactions" Nuclear Medicine & biology, 1999, vol. 26, pp. 883-890.

* cited by examiner

PEPTIDE-BASED COMPOUNDS

This application is a continuation of U.S. application Ser. No. 12/423,953 filed Apr. 15, 2009, now U.S. Pat. No. 7,994,134, which is a division of U.S. application Ser. No. 10/753,729 filed Jan. 8, 2004, now U.S. Pat. No. 7,521,419, which is a continuation application of international application number PCT/NO02/00250 filed Jul. 8, 2002, which claims priority to Great Britain application number 0116815.2 filed Jul. 10, 2001 and to Norwegian application number 20014954 filed Oct. 11, 2001, the entire disclosure of which is hereby incorporated by reference.

FIELD OF INVENTION

The present invention relates to new peptide-based compounds and their use in therapeutically effective treatments as well as for diagnostic imaging techniques. More specifically the invention relates to the use of such peptide-based compounds as targeting vectors that bind to receptors associated with angiogenesis, in particular integrin receptors, e.g. the αvβ3 integrin receptor. Such contrast agents may thus be used for diagnosis of for example malignant diseases, heart diseases, endometriosis, inflammation-related diseases, rheumatoid arthritis and Kaposi's sarcoma. Moreover such agents may be used in therapeutic treatment of these diseases.

BACKGROUND OF INVENTION

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumors must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infarcted parts of the myocardium, which occurs if a stenosis is released within a short time.

Further examples of undesired conditions that are associated with neovascularization or angiogenesis, the development or proliferation of new blood vessels are shown below. Reference is also made in this regard to WO 98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous alformations, astrocytomas, choriocarcinomas, glioblastomas, gliomas, hemangiomas (childhood, capillary), hepatomas, hyperplastic endometrium, ischemic myocardium, endometriosis, Kaposi sarcoma, macular degeneration, melanoma, neuroblastomas, occluding peripheral artery disease, osteoarthritis, psoriasis, retinopathy (diabetic, proliferative), scleroderma, seminomas and ulcerative colitis.

Angiogenesis involves receptors that are unique to endothelial cells and surrounding tissues. These markers include growth factor receptors such as VEGF and the Integrin family of receptors. Immunohistochemical studies have demonstrated that a variety of integrins perhaps most importantly the $\alpha_v$ class are expressed on the apical surface of blood vessels [Conforti, G., et al. (1992) Blood 80: 37-446] and are available for targeting by circulating ligands [Pasqualini, R., et al. (1997) Nature Biotechnology 15: 542-546]. The α5β1 is also an important integrin in promoting the assembly of fibronectin matrix and initiating cell attachment to fibronectin. It also plays a crucial role in cell migration [Bauer, J. S., (1992) J. Cell Biol. 116: 477-487] as well as tumour invasion and metastasis [Gehlsen, K. R., (1988) J. Cell Biol. 106: 925-930].

The integrin αvβ3 is one of the receptors that is known to be associated with angiogenesis. Stimulated endothelial cells appear to rely on this receptor for survival during a critical period of the angiogeneic process, as antagonists of the αvβ3 integrin receptor/ligand interaction induce apoptosis and inhibit blood vessel growth.

Integrins are heterodimeric molecules in which the α- and β-subunits penetrate the cell-membrane lipid bilayer. The α-subunit has four $Ca^{2+}$ domains on its extracellular chain, and the β-subunit has a number of extracellular cysteine-rich domains.

Many ligands (eg. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. (Ruoslahti, J. Clin. Invest., 87: 1-5 (1991)). Perhaps the most widely studied effect of RGD peptides and mimetics thereof relate to their use as anti-thrombotic agents where they target the platelet integrin GpIIbIIIa.

Inhibition of angiogenesis in tissues by administration of either an αvβ3 or αvβ5 antagonist has been described in for example WO 97/06791 and WO 95/25543 using either antibodies or RGD containing peptides. EP 578083 describes a series of mono-cyclic RGD containing peptides and WO 90/14103 claims RGD-antibodies. Haubner et al. in the J. Nucl. Med. (1999); 40: 1061-1071 describe a new class of tracers for tumour targeting based on monocyclic RGD containing peptides. Biodistribution studies using whole-body autoradiographic imaging revealed however that the $^{125}$I-labelled peptides had very fast blood clearance rates and predominantly hepatobiliary excretion routes resulting in high background.

Cyclic RGD peptides containing multiple bridges have also been described in WO 98/54347 and WO 95/14714. Peptides derived from in vivo biopanning (WO 97/10507) have been used for a variety of targeting applications. The sequence CDCRGDCFC (RGD-4C), has been used to target drugs such as doxirubicin (WO 98/10795), nucleic acids and adenoviruses to cells (see WO 99/40214, WO 99/39734, WO 98/54347, WO 98/54346, U.S. Pat. No. 5,846,782). Peptides containing multiple cysteine residues do however suffer from the disadvantage that multiple disulphide isomers can occur. A peptide with 4 cysteine residues such as RGD-4C has the possibility of forming 3 different disulphide folded forms. The isomers will have varying affinity for the integrin receptor as the RGD pharmacophore is forced into 3 different conformations.

Further examples of RGD comprising peptide-based compounds are found in PCT/NO01/00146 and PCT/NO01/00390, the content of which are incorporated herein by reference.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background. These stringent conditions are met by the bicyclic structures described in the present invention.

SUMMARY OF THE INVENTION

In one aspect, the invention provides new peptide-based compound of Formula I as defined in the claims. These compounds have affinity for integrin receptors, e.g. affinity for the integrin αvβ3.

The present invention also provides a pharmaceutical composition comprising an effective amount (e.g. an amount effective for enhancing image contrast in in vivo imaging) of a compound of general formula I or a salt thereof, together with one or more pharmaceutically acceptable adjuvants, excipients or diluents.

The invention further provides a pharmaceutical composition for treatment of a disease comprising an effective amount of a compound of general formula I, or an acid addition salt thereof, together with one or more pharmaceutically acceptable adjuvants, excipients or diluents.

In a further embodiment of this invention, the use of radio-isotopes of iodine or fluorine is specifically contemplated. These species can be used in therapeutic and diagnostic imaging applications. While, at the same time, a metal attached to a chelating agent on the same peptide-linker can also be used in either therapeutic or diagnostic imaging applications.

Use of the compounds of formula I in the manufacture of therapeutic compositions (medicament) and in methods of therapeutic or prophylactic treatment, preferably treatment of cancer, of the human or animal body are thus considered to represent further aspects of the invention.

Viewed from a further aspect the invention provides the use of a compound of formula I for the manufacture of a contrast medium for use in a method of diagnosis involving administration of said contrast medium to a human or animal body and generation of an image of at least part of said body.

Viewed from a still further aspect the invention provides a method of generating an image of a human or animal body involving administering a contrast agent to said body, e.g. into the vascular system and generating an image of at least a part of said body to which said contrast agent has distributed using scintigraphy, PET or SPECT modalities, wherein as said contrast agent is used an agent of formula I.

Viewed from a still further aspect the invention provides a method of generating enhanced images of a human or animal body previously administered with a contrast agent composition comprising a compound as defined by formula I, which method comprises generating an image of at least part of said body.

Viewed from a further aspect the invention provides a method of monitoring the effect of treatment of a human or animal body with a drug to combat a condition associated with cancer, preferably angiogenesis, e.g. a cytotoxic agent, said method involving administering to said body an agent of formula I and detecting the uptake of said agent by cell receptors, preferably endothelial cell receptors and in particular αvβ3 receptors, said administration and detection optionally but preferably being effected repeatedly, e.g. before, during and after treatment with said drug.

DETAILED DESCRIPTION OF THE PREFERRED EMBODIMENTS OF THE INVENTION

Viewed from one aspect the invention provides new peptide-based compounds of Formula I as defined in the claims. These compounds have affinity for integrin receptors, e.g. affinity for the integrin αvβ3.

The compounds of Formula I comprise at least two bridges, wherein one bridge forms a disulphide bond and the second bridge comprises a thioether (sulphide) bond and wherein the bridges fold the peptide moiety into a 'nested' configuration.

The compounds of the current invention thus have a maximum of one disulphide bridge per molecule moiety. Compounds defined by the present invention are surprisingly stable in vivo and under the conditions employed during labelling, e.g. during labelling with technetium.

These new compounds may be used in therapeutically effective treatments as well as for imaging purposes.

The new peptide-based compounds described in the present invention are defined by Formula I:

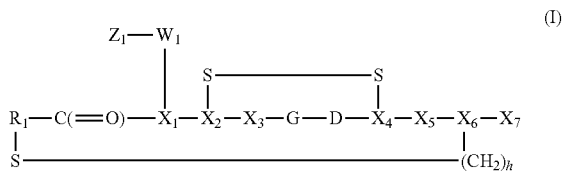

or physiologically acceptable salts thereof
wherein
G represents glycine, and
D represents aspartic acid, and
$R_1$ represents —$(CH_2)_n$— or —$(CH_2)_n$—$C_6H_4$—, preferably $R_1$ represents —$(CH_2)$—, and n represents a positive integer between 1 and 10, and h represents a positive integer 1 or 2, and $X_1$ represents an amino acid residue wherein said amino acid possesses a functional side-chain such as an acid or amine preferentially aspartic or glutamic acid, lysine, homolysine, diaminoalcylic acid or diaminopropionic acid, $X_2$ and $X_4$ represent independently an amino acid residue capable of forming a disulphide bond, preferably a cysteine or a homocysteine residue, and $X_3$ represents arginine, N-methylarginine or an arginine mimetic, preferably an arginine, and $X_5$ represents a hydrophobic amino acid or derivatives thereof, preferably a tyrosine, a phenylalanine, a 3-iodo-tyrosine or a naphthylalanine residue, and more preferably a phenylalanine or a 3-iodo-tyrosine residue, and $X_6$ represents a thiol-containing amino acid residue, preferably a cysteine or a homocysteine residue, and $X_7$ is absent or represents a homogeneous biomodifier moiety preferably based on a monodisperse PEG building block comprising 1 to 10 units of said building block, said biomodifier having the function of modifying the pharmacokinetics and blood clearance rates of the said agents.

In addition $X_7$ may also represent 1 to 10 amino acid residues preferably glycine, lysine, aspartic acid or serine. In a preferred embodiment of this invention $X_7$ represents a biomodifier unit comprised of polymerisation of the monodisperse PEG-like structure, 17-amino-5-oxo-6-aza-3,9,12,15-tetraoxaheptadecanoic acid of Formula II,

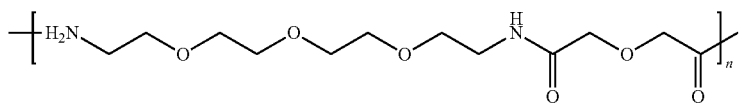

(II)

wherein n equals an integer from 1 to 10 and where the C-terminal unit is an amide moiety.

$W_1$ is absent or represents a spacer moiety and is preferentially derived from glutaric and/or succinic acid and/or a polyethyleneglycol based unit and/or a unit of Formula II $Z_1$ is an antineoplastic agent, a chelating agent or a reporter moiety that can be represented by a chelating agent of Formula III

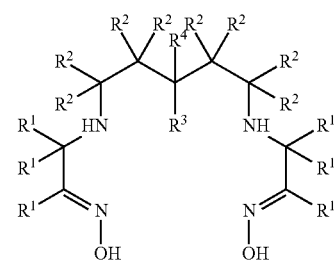

(III)

where:

each $R^1$, $R^2$, $R^3$ and $R^4$ is independently an R group;

each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring, or can represent a chelating agent given by formulas a, b, c and d.

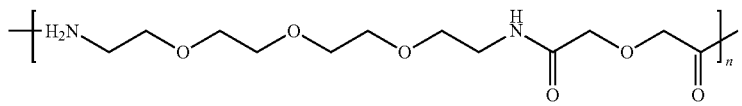

(II)

a

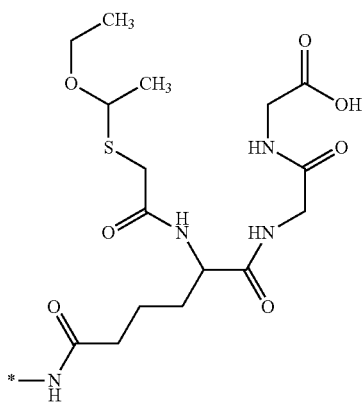

b

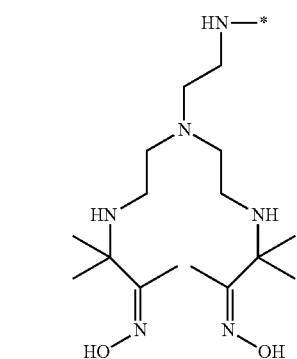

c

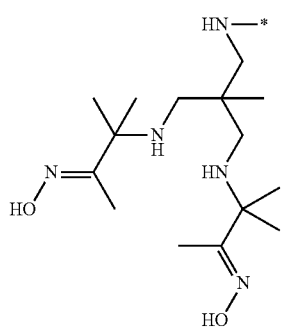

d

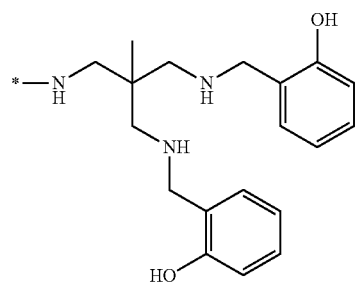

A preferred example of a chelating agent is represented by formula e.

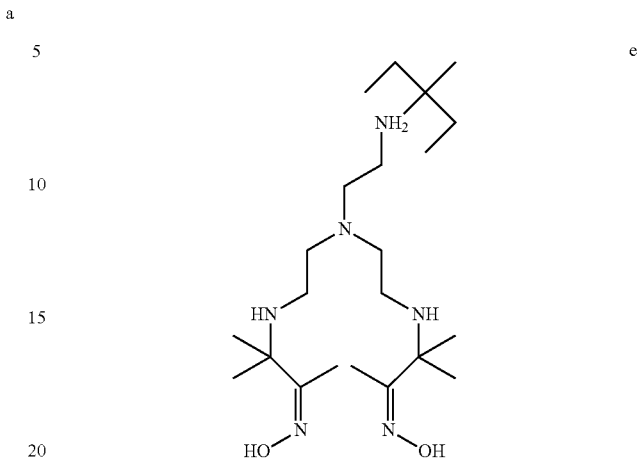

e

Conjugates comprising chelating agents of Formula III can be radiolabelled to give good radiochemical purity, RCP, at room temperature, under aqueous conditions at near neutral pH. The risk of opening the disulphide bridges of the peptide component at room temperature is less than at an elevated temperature. A further advantage of radiolabelling the conjugates at room temperature is a simplified procedure in a hospital pharmacy.

The role of the spacer moiety $W_1$ is to distance the relatively bulky chelating agent from the active site of the peptide component. The spacer moiety $W_1$ is also applicable to distance a bulky antineoplastic agent from the active site of the peptide.

It is found that the biomodifier, $X_7$, modifies the pharmacokinetics and blood clearance rates of the compounds. The biomodifier effects less uptake of the compounds in tissue i.e. muscle, liver etc. thus giving a better diagnostic image due to less background interference. The secretion is mainly through the kidneys due to a further advantage of the biomodifier.

However the compounds defined in Formula I may also comprise chelating agents, Z1, as defined in Table I.

In some aspects of the invention, $Z_1$ comprises a reporter moiety where said reporter moiety comprises a radionuclide. Further definitions of chelating agents are listed in the following Table I.

TABLE I

| Class of ligand | Structure | Definitions |
|---|---|---|
| Amine-oxime | (structure with $Y_1$–$Y_8$, X, m', n') | Y1-8 and be H, alkyl, aryl or combinations thereof and Y4 or Y5 contains a suitable functionality such that it can be conjugated to the peptide vector- e.g. preferably alkylamine, alkysulphide, alkoxy, alkyl carboxylate, arylamine, aryl sulphide or α-haloacetyl X = C or N when m' = n' = 1 X = N when m' = n' = 2 |

TABLE I-continued

| Class of ligand | Structure | Definitions |
|---|---|---|
| MAG3 type | [structure] | P = protecting group (preferably. benozyl, acetyl, EOE); Y1, Y2 contains a suitable functionality such that it can be conjugated to the peptide vector; preferably H (MAG3), or the side chain of any amino acid, in either L or D form. |
| G4 type ligands | [structure] | Y1, Y2, Y3-contains a suitable functionality such that it can be conjugated to the peptide vector; preferably H, or the side chain of any amino acid, in either L or D form. |
| Tetra-amine ligands | [structure] | Y1-Y-6 can be H, alkyl, aryl or combinations thereof where the Y1-6 groups contain one or more functional moieties such that the chelate can be conjugated to the vector- e.g. preferably alkylamine, alkylsulphide, alkoxy, alkyl carboxylate, arylamine, aryl sulphide or α-haloacetyl |
| Cylam type ligands | [structure] | Y1-5 can be H, alkyl, aryl or combinations thereof and where Y1-5 groups contain one or more functional moieties such that the chelate can be conjugated to the vector- e.g. preferably alkylamine, alkylsulphide, alkoxy, alkyl carboxylate, arylamine, aryl sulphide or α-haloacetyl |
| Diamine-diphenol | [structure] | Y1, Y2-H, alkyl, aryl and where Y1 or Y2 groups contains a functional moiety such that the chelate can be conjugated to the vector-e.g. preferably alkylamine, alkylsulfphide, alkoxy, alkyl carboxylate, arylamine, aryl sulphide or α-haloacetyl W = C, N m' = n' = 1 or 2 |
| HYNIC | [structure] | V = linker to vector or vector itself. |
| Amide thiols | [structure] | P = protecting group (preferably. benzoyl, acetyl, EOE); Y1-5 = H, alkyl, aryl; or Y3 is a L or D amino acid side-chain or glycine. and the carboxylate may be used for conjugation to the vector via an amide bond. Alternatively the $R_{1-5}$ groups may contain additional functionality such that the chelate can be conjugated to the vector- e.g. alkylamine, alkylsulphide, alkoxy, alkyl carboxylate, arylamine, aryl sulphide or α-haloacetyl. |

In some aspects of the invention of Formula I the $Z_1$ moiety comprises the binding of a $^{18}F$ isotope or an isotope of Cu, incorporation into the agent either as a prosthetic group or by substitution or addition reactions. The resulting compound may thus be used in Positron Emission Tomography (PET) Imaging.

In one aspect of the present invention of formula I $Z_1$ is represented by an antineoplastic agent. In this aspect the compound will target an angiogenic site associated with cancer and bring the antineoplastic agent to the diseased area.

The antineoplastic agent may be represented by cyclophosphamide, chloroambucil, busulphan, methotrexate, cytarabine, fluorouracil, vinblastine, paclitaxel, doxorubicin, daunorubicin, etoposide, teniposide, cisplatin, amsacrine, docetaxel, but a wide range of other antineoplastic agents may also be used.

The peptide component of the conjugates described herein have preferably no free amino- or carboxy-termini. This introduces into these compounds a significant increase in resistance against enzymatic degradation and as a result they have an increased in vivo stability as compared to many known free peptides.

As used herein the term 'amino acid' refers in its broadest sense to proteogenic L-amino acids, D-amino acids, chemically modified amino acids, N-methyl, Cα-methyl and amino acid side-chain mimetics and unnatural amino acids such as naphthylalanine. Any naturally occurring amino acid or mimetics of such natural occurring amino acids are preferred.

Some preferred embodiments of the compounds of formula I are illustrated by compounds I-IV below:

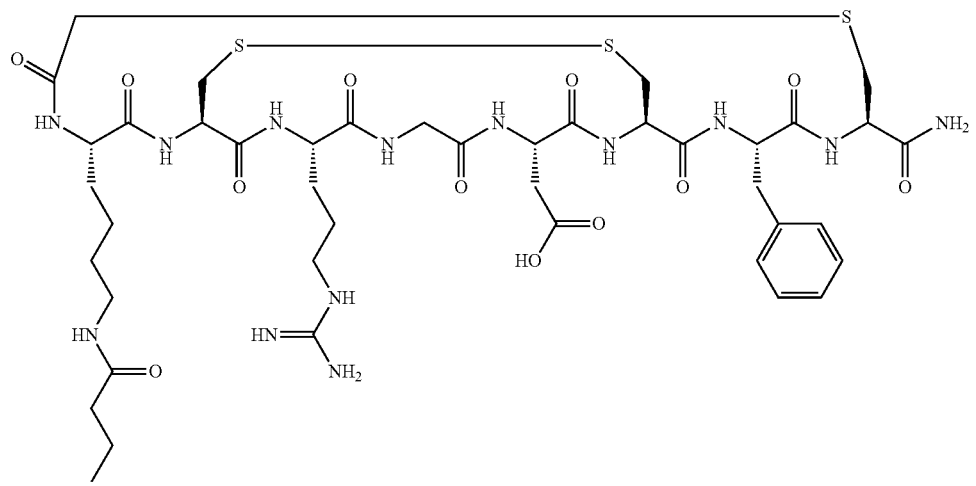
Compound I
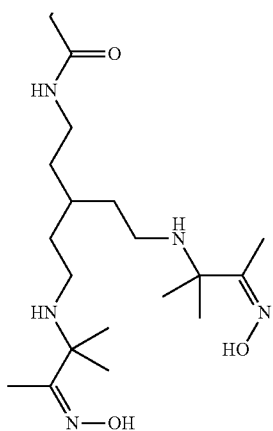
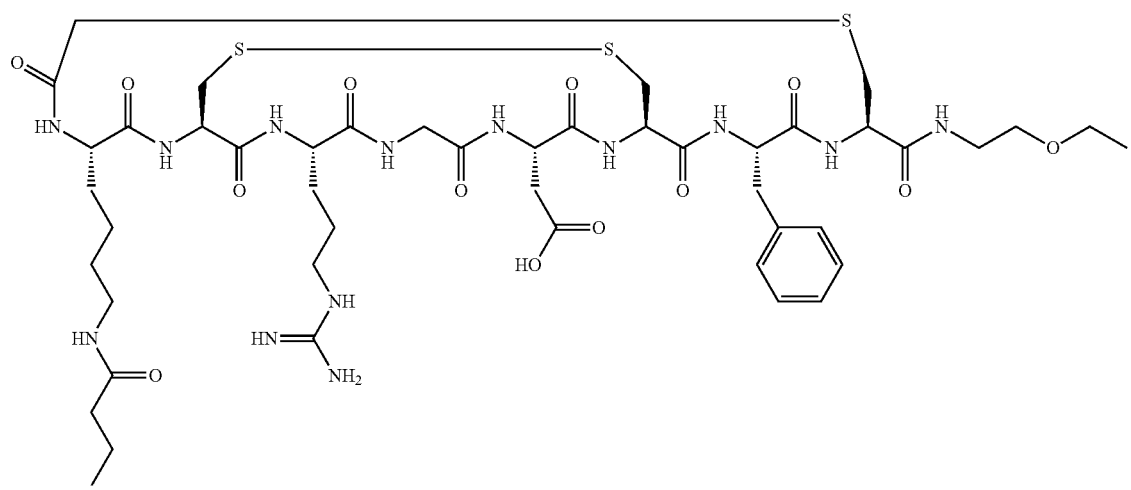
Compound II

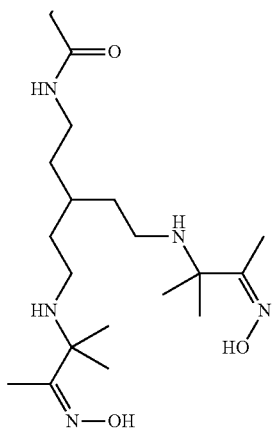
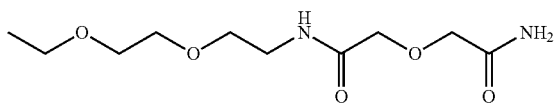
Compound III
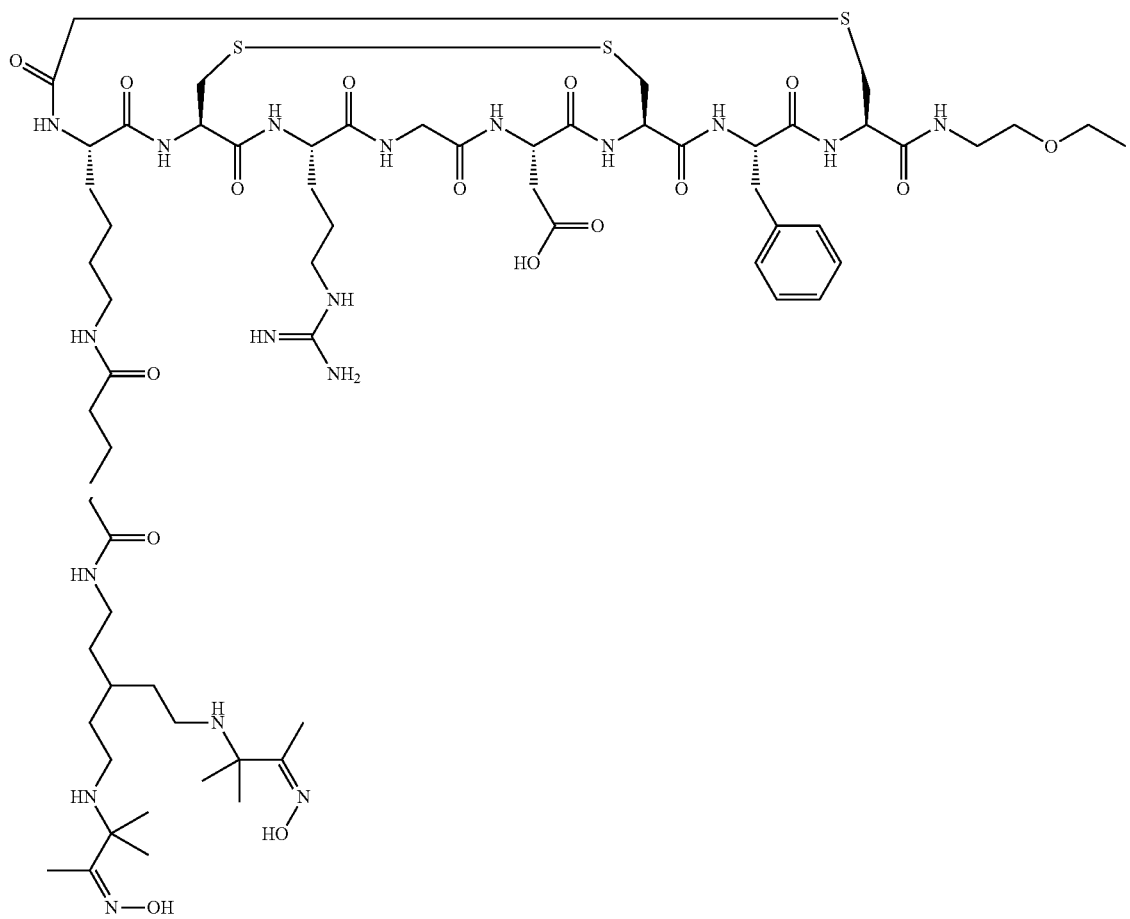

-continued
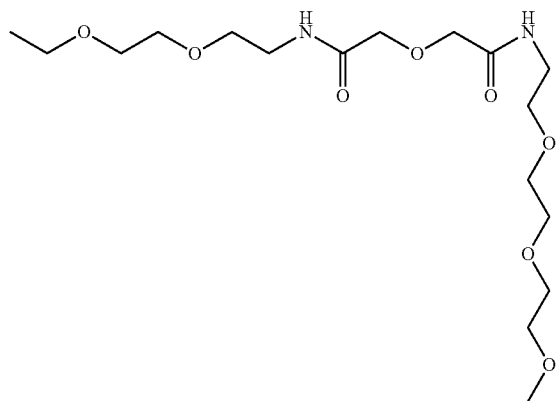
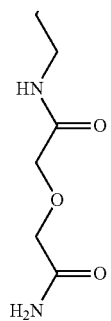
Compound IV
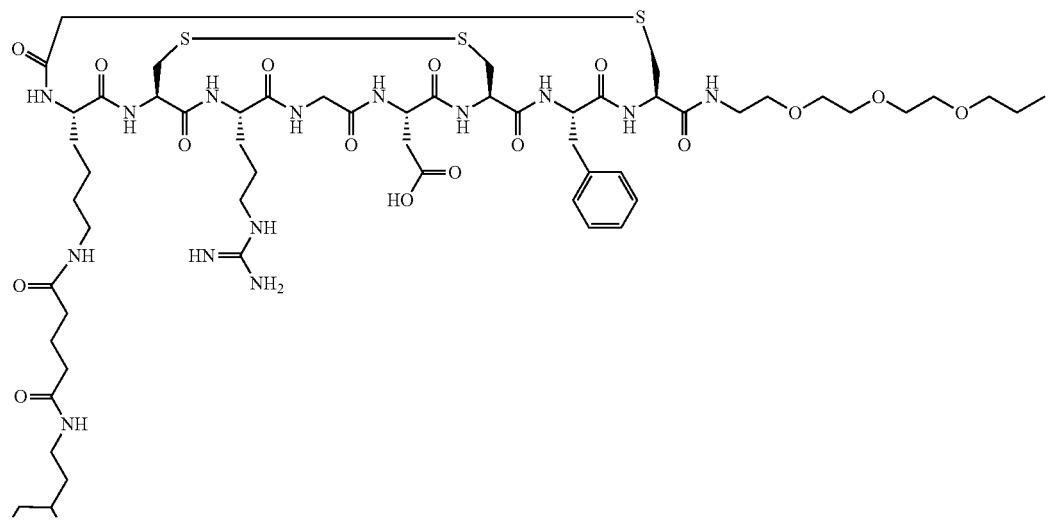
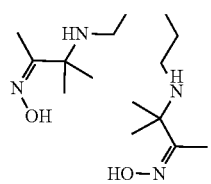

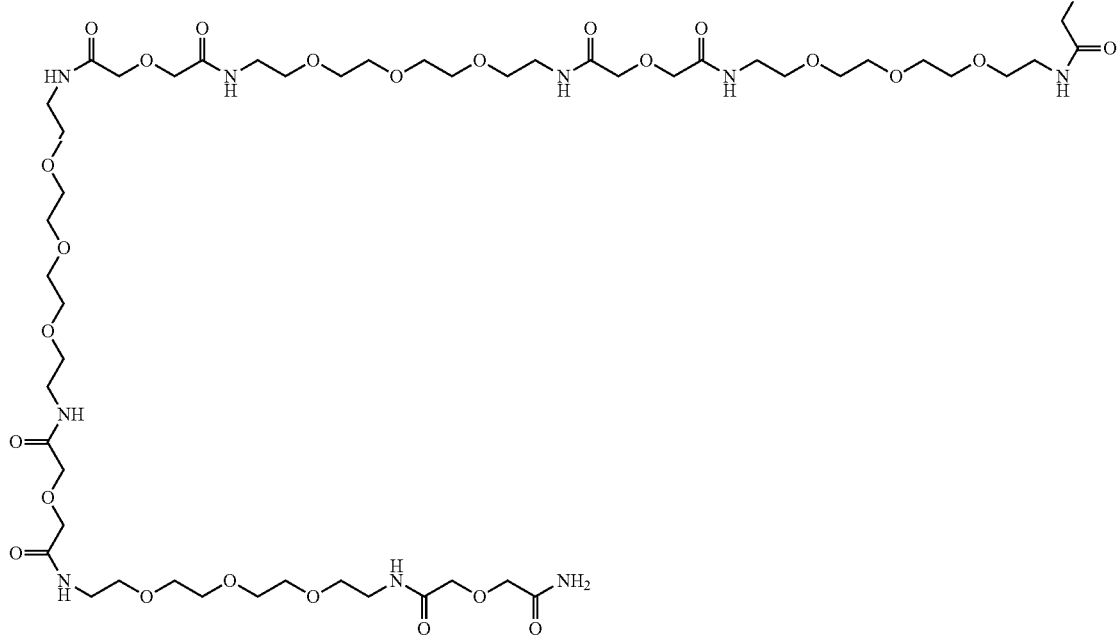

In most cases, it is preferred that the amino acids in the peptide are all in the L-form. However, in some embodiments of the invention one, two, three or more of the amino acids in the peptide are preferably in the D-form. The inclusion of such D-form amino acids can have a significant effect on the serum stability of the compound.

According to the present invention, any of the amino acid residues as defined in formula I may preferably represent a naturally occurring amino acid and independently in any of the D or L conformations.

Some of the compounds of the invention are high affinity RGD based vectors. As used herein the term 'high affinity RGD based vector' refers to compounds that have a Ki of <10 nM and preferably <5 nM, in a competitive binding assay for $\alpha v \beta 3$ integrin and where the Ki value was determined by competition with the known high affinity ligand echistatin. Methods for carrying out such competition assays are well known in the art.

The present invention also provides a pharmaceutical composition comprising an effective amount (e.g. an amount effective for enhancing image contrast in in vivo imaging) of a compound of general formula I or a salt thereof, together with one or more pharmaceutically acceptable adjuvants, excipients or diluents.

The invention further provides a pharmaceutical composition for treatment of a disease comprising an effective amount of a compound of general formula I, or an acid addition salt thereof, together with one or more pharmaceutically acceptable adjuvants, excipients or diluents.

Other representative spacer ($W_1$) elements include structural-type polysaccharides, storage-type polysaccharides, polyamino acids and methyl and ethyl esters thereof, and polypeptides, oligosaccharides and oligonucleotides, which may or may not contain enzyme cleavage sites.

The reporter moieties ($Z_1$) in the contrast agents of the invention may be any moiety capable of detection either directly or indirectly in an in vivo diagnostic imaging procedure. Preferably the contrast agent comprises one reporter. Preferred are moieties which emit or may be caused to emit detectable radiation (e.g. by radioactive decay).

For MR imaging the reporter will either be a non zero nuclear spin isotope (such as $^{19}F$) or a material having unpaired electron spins and hence paramagnetic, superparamagnetic, ferrimagnetic or ferromagnetic properties; for light imaging the reporter will be a light scatterer (e.g. a coloured or uncoloured particle), a light absorber or a light emitter; for magnetometric imaging the reporter will have detectable magnetic properties; for electrical impedance imaging the reporter will affect electrical impedance; and for scintigraphy, SPECT, PET, and the like, the reporter will be a radionuclide.

Stated generally, the reporter may be (1) a chelatable metal or polyatomic metal-containing ion (i.e. TcO, etc), where the metal is a high atomic number metal (e.g. atomic number greater than 37), a paramagentic species (e.g. a transition metal or lanthanide), or a radioactive isotope, (2) a covalently bound non-metal species which is an unpaired electron site (e.g. an oxygen or carbon in a persistant free radical), a high atomic number non-metal, or a radioisotope, (3) a polyatomic cluster or crystal containing high atomic number atoms, displaying cooperative magnetic behaviour (e.g. superparamagnetism, ferrimagnetism or ferromagnetism) or containing radionuclides.

Examples of particular preferred reporter groups ($Z_1$) are described in more detail below.

Chelated metal reporters are preferably chosen from the group below; $^H Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$.

The metal ions are desirably chelated by chelant groups on the linker moiety. Further examples of suitable chelant groups are disclosed in U.S. Pat. No. 4,647,447, WO89/00557, U.S. Pat. No. 5,367,080, U.S. Pat. No. 5,364,613.

Methods for metallating any chelating agents present are within the level of skill in the art. Metals can be incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so as not to interfere with the binding of the metal ion with the chelating agent. The chelating agent-containing moiety is preferrably in aqueous solution at a pH of between about 5 and about 9, more preferably between pH about 6 to about 8. The chelating agent-containing moiety can be mixed with buffer salts such as citrate, carbonate, acetate, phosphate and borate to produce the optimum pH. Preferably, the buffer salts are selected so as not to interfere with the subsequent binding of the metal ion to the chelating agent.

The following isotopes or isotope pairs can be used for both imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

Preferred non-metal atomic reporters include radioisotopes such as $^{123}I$, $^{131}I$ and $^{18}F$ as well as non zero nuclear spin atoms such as $^{19}F$, and heavy atoms such as I.

In a further embodiment of this invention, the use of radioisotopes of iodine or fluorine is specifically contemplated. For example, if the peptide or linker is comprised of substituents that can be chemically substituted by iodine or fluorine in a covalent bond forming reaction, such as, for example, substituents containing hydroxyphenyl or p-nitrobenzoyl functionality, such substituents can be labeled by methods well known in the art with a radioisotope of iodine or fluorine respectively. These species can be used in therapeutic and diagnostic imaging applications. While, at the same time, a metal attached to a chelating agent on the same peptide-linker can also be used in either therapeutic or diagnostic imaging applications.

A preferred embodiment of the invention relates to a radiolabelled agent of general formula (I), particularly for use in tumour imaging.

The diagnostic agents of the invention may be administered to patients for imaging in amounts sufficient to yield the desired contrast with the particular imaging technique. Where the reporter is a metal, generally dosages of from 0.001 to 5.0 mmoles of chelated imaging metal ion per kilogram of patient bodyweight are effective to achieve adequate contrast enhancements. Where the reporter is a radionuclide, dosages of 0.01 to 100 mCi, preferably 0.1 to 50 mCi will normally be sufficient per 70 kg bodyweight.

The dosage of the compounds of the invention for therapeutic use will depend upon the condition being treated, but in general will be of the order of from 1 pmol/kg to 1 mmol/kg bodyweight.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

The compounds of formula I may be therapeutically effective in the treatment of disease states as well as detectable in in vivo imaging. Thus for example the vector on the reporter moieites may have therapeutic efficacy, e.g. by virtue of the radiotherapeutic effect of a radionuclide reporter of the vector moiety.

Use of the compounds of formula I in the manufacture of therapeutic compositions (medicament) and in methods of therapeutic or prophylactic treatment, preferably treatment of cancer, of the human or animal body are thus considered to represent further aspects of the invention.

Further examples of the reporters which may be used in the context of the current application are given on pages 63-66 and 70-86 of WO98/47541 and the disclosures made on these pages are incorporated herein by reference in their entirety. It is hereby asserted that each and every reporter or part thereof disclosed on the aforementioned pages is considered to be part of the description of the invention contained in this application.

Viewed from a further aspect the invention provides the use of a compound of formula I for the manufacture of a contrast medium for use in a method of diagnosis involving administration of said contrast medium to a human or animal body and generation of an image of at least part of said body.

Viewed from a still further aspect the invention provides a method of generating an image of a human or animal body involving administering a contrast agent to said body, e.g. into the vascular system and generating an image of at least a part of said body to which said contrast agent has distributed using scintigraphy, PET or SPECT modalities, wherein as said contrast agent is used an agent of formula I.

Viewed from a still further aspect the invention provides a method of generating enhanced images of a human or animal body previously administered with a contrast agent composition comprising a compound as defined by formula I, which method comprises generating an image of at least part of said body.

Viewed from a further aspect the invention provides a method of monitoring the effect of treatment of a human or animal body with a drug to combat a condition associated with cancer, preferably angiogenesis, e.g. a cytotoxic agent, said method involving administering to said body an agent of formula I and detecting the uptake of said agent by cell receptors, preferably endothelial cell receptors and in particular αvβ3 receptors, said administration and detection optionally but preferably being effected repeatedly, e.g. before, during and after treatment with said drug.

The compounds of the present invention can be synthesised using all the known methods of chemical synthesis but particularly useful is the solid-phase methodology of Merrifield employing an automated peptide synthesiser (J. Am. Chem. Soc., 85: 2149 (1964)). The peptides and peptide chelates may be purified using high performance liquid chromatography (HPLC) and characterised by mass spectrometry and analytical HPLC before testing in the in vitro screen.

The present invention will now be further illustrated by way of the following non-limiting examples.

EXAMPLES

Example 1

Synthesis of disulfide [Cys$^{2-6}$] thioether cyclo [CH$_2$CO-Lys(cPn216-glutaryl)-Cys$^2$-Arg-Gly-Asp-Cys$^6$-Phe-Cys]-NH$_2$ (SEQ ID NO. 1)

1 a) Synthesis of cPn216 Chelate

For details of the synthesis of technetium chelate cPn216 the reader is referred to patent filing GB0116815.2

1 b) Synthesis of cPn216-Glutaric Acid Intermediate cPn216 (100 mg, 0.29 mmol) was dissolved in DMF (10 mL) and glutaric anhydride (33 mg, 0.29 mmol) added by portions with stirring. The reaction was stirred for 23 hours to afford complete conversion to the desired product. The pure acid was obtained following RP-HPLC in good yield.

1 c) Synthesis of tetrafluorothiophenyl ester of cPn216-glutaric acid

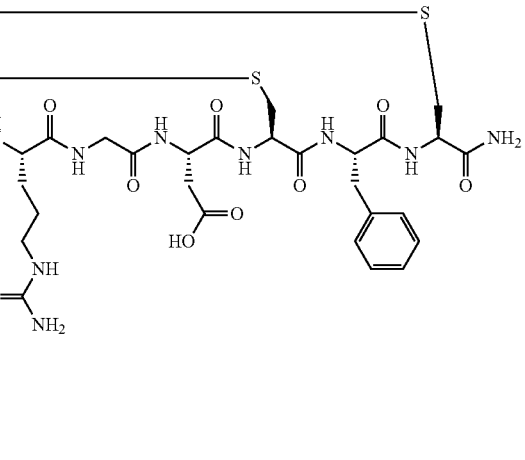

Molecular Weight = 1407.754
Exact Mass = 1406.662
Molecular Formula = C60H98N18O15S3

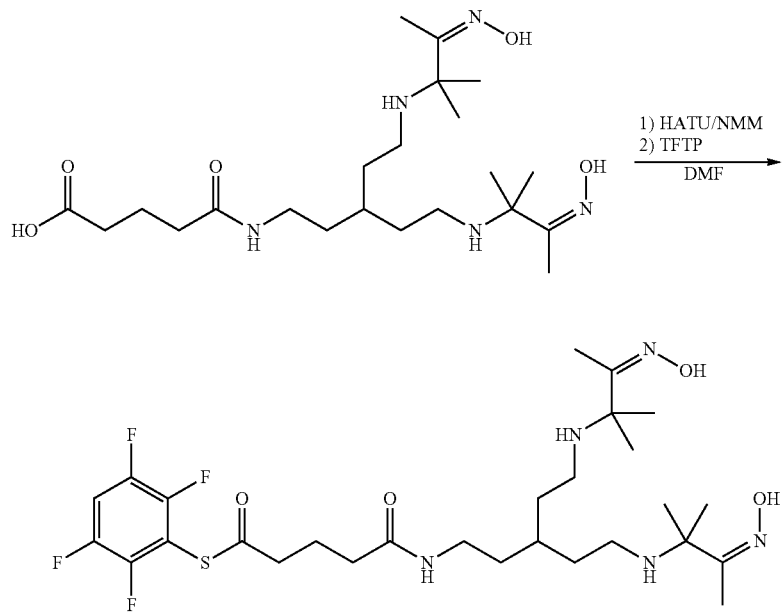

To cPn216-glutaric acid (300 mg, 0.66 mmol) in DMF (2 mL) was added HATU (249 mg, 0.66 mmol) and NMM (132 μL, 1.32 mmol). The mixture was stirred for 5 minutes then tetrafluorothiophenol (0.66 mmol, 119 mg) was added. The solution was stirred for 10 minutes then the reaction mixture was diluted with 20% acetonitrile/water (8 mL) and the product purified by RP-HPLC yielding 110 mg of the desired product following freeze-drying.

1 d) Synthesis of ClCH$_2$CO-Lys-Cys(tBu)-Arg-Gly-Asp-Cys(tBu)-Phe-Cys-NH$_2$ (SEQ ID NO. 1)

The peptide was synthesised on an ABI 433A automatic peptide synthesiser starting with Rink Amide AM resin on a 0.25 mmol scale using 1 mmol amino acid cartridges. The amino acids were pre-activated using HBTU before coupling. N-terminal amine groups were chloroacetylated using a solution of chloroacetic anhydride in DMF for 30 min.

The simultaneous removal of peptide and side-chain protecting groups (except tBu) from the resin was carried out in TFA containing TIS (5%), H$_2$0 (5%) and phenol (2.5%) for two hours.

After work-up 295 mg of crude peptide was obtained (Analytical HPLC: Gradient, 5-50% B over 10 min where A=H$_2$O/ 0.1% TFA and B=CH$_3$CN/0.1% TFA; column, Phenomenex Luna 3μ C18 (2) 50×4.6 mm; flow, 2 mL/min; detection, UV 214 nm; product retention time, 6.42 min). Further product

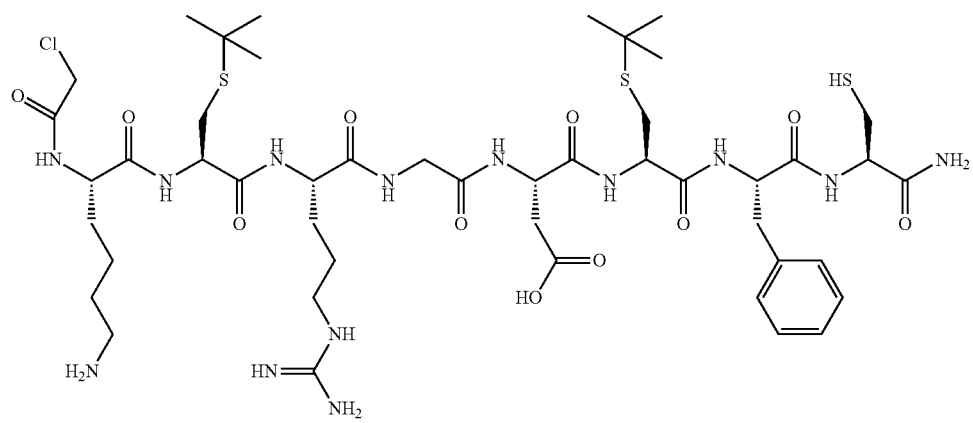

Molecular Weight = 1118.844
Exact Mass = 1117.464
Molecular Formula = C46H76ClN13O11S3 characterisation was carried out using mass spectrometry: Expected, M+H at 1118.5, found, at 1118.6).

1 e) Synthesis of thioether cyclo[CH₂CO-Lys-Cys(tBu)-Arg-Gly-Asp-Cys(tBu)-Phe-Cys]-NH₂ (SEQ ID NO. 1)

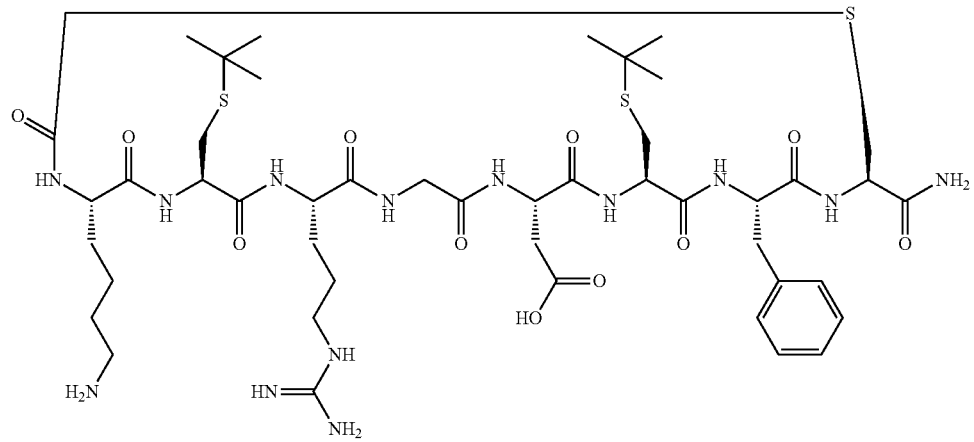

Molecular Weight = 1082.383
Exact Mass = 1081.487
Molecular Formula = C46H75N13O11S3

295 mg of ClCH₂CO-Lys-Cys(tBu)-Arg-Gly-Asp-Cys(tBu)-Phe-Cys-NH₂ (SEQ ID NO. 1) was dissolved in water/acetonitrile. The mixture was adjusted to pH 8 with ammonia solution and stirred for 16 hours.

After work-up 217 mg of crude peptide was obtained (Analytical HPLC: Gradient, 5-50% B over 10 min where A=H₂O/0.1% TFA and B=CH₃CN/0.1% TFA; column, Phenomenex Luna 3μ C18 (2) 50×4.6 mm; flow, 2 mL/min; detection, UV 214 nm; product retention time, 6.18 min). Further product characterisation was carried out using mass spectrometry: Expected, M+H at 1882.5, found, at 1882.6).

1 f) Synthesis of Disulphide [Cys$^{2-6}$] thioether cyclo [CH₂CO-Lys-Cys$^2$-Arg-Gly-Asp-Cys$^6$-Phe-Cys]-NH₂ (SEQ ID NO. 1)

217 mg of thioether cyclo[CH₂CO-Lys-Cys(tBu)-Arg-Gly-Asp-Cys(tBu)-Phe-Cys]-NH₂ (SEQ ID NO. 1) was treated with a solution of anisole (500 μL), DMSO (2 mL) and TFA (100 mL) for 60 min following which the TFA was removed in vacuo and the peptide precipitated by the addition of diethyl ether.

Purification by preparative HPLC (Phenomenex Luna 10μ C18 (2) 250×50 mm column) of the crude material (202 mg) was carried out using 0-30% B, where A=H₂O/0.1% TFA and B=CH₃CN/0.1% TFA, over 60 min at a flow rate of 50 mL/min. After lyophilisation 112 mg of pure material was obtained (Analytical HPLC: Gradient, 5-50% B over 10 min where A=H₂O/0.1% TFA and B=CH₃CN/0.1% TFA; column, Phenomenex Luna 3μ C18 (2) 50×4.6 mm; flow, 2 mL/min; detection, UV 214 nm; product retention time, 5.50 min). Further product characterisation was carried out using mass spectrometry: Expected, M+H at 968, found, at 971).

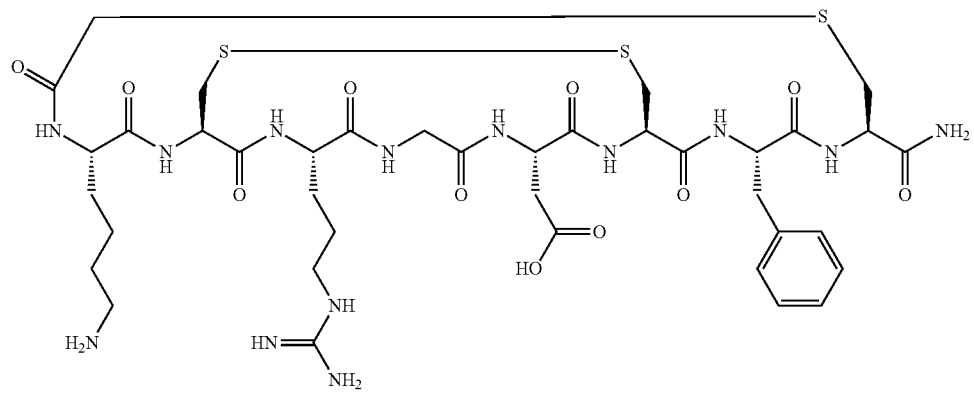

Molecular Weight = 968.150
Exact Mass = 967.346
Molecular Formula = C38H57N13O11S3

1 g) Synthesis of disulfide [Cys$^{2-6}$] thioether cyclo[CH$_2$CO-Lys(cPn216-glutaryl)-Cys$^2$-Arg-Gly-Asp-Cys$^6$-Phe-Cys]-NH$_2$ (SEQ ID NO. 1)

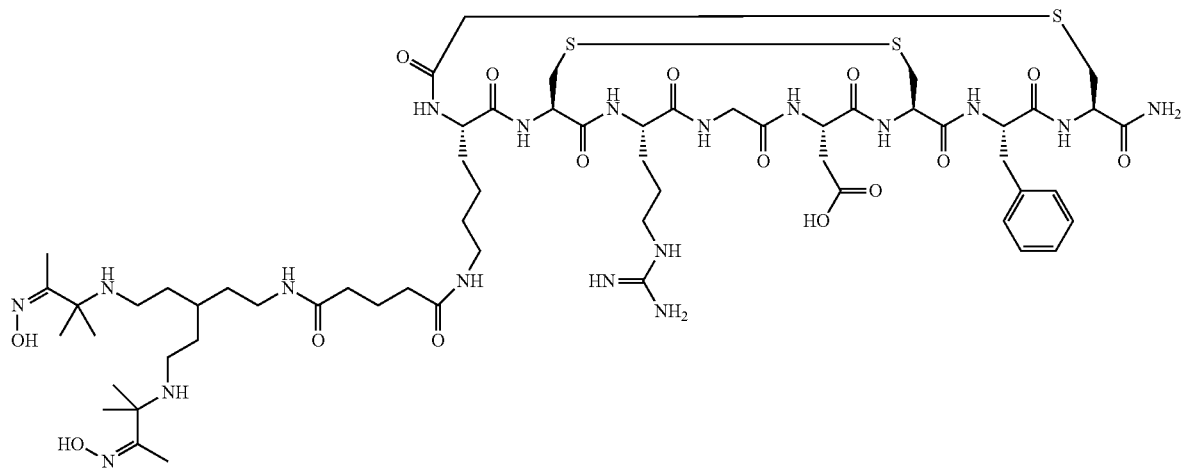

Molecular Weight = 1407.754
Exact Mass = 1406.662
Molecular Formula = C60H98N18O15S3

9.7 mg of disulphide[Cys$^{2-6}$] thioether cyclo[CH$_2$CO-Lys-Cys-Arg-Gly-Asp-Cys-Phe-Cys]-NH$_2$, (SEQ ID NO. 1) 9.1 mg of cPn216 chelate active ester and 6 µL of N-methylmorpholine was dissolved in DMF (0.5 mL). The mixture was stirred for 3 hours.

Purification by preparative HPLC (Phenomenex Luna 5µ C18 (2) 250×21.20 mm column) of the reaction mixture was carried out using 0-30% B, where A=H$_2$O/0.1% TFA and B=CH$_3$CN/0.1% TFA, over 40 min at a flow rate of 10 mL/min. After lyophilisation 5.7 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 7.32 min). Further product characterisation was carried out using mass spectrometry: Expected, M+H at 1407.7, found, at 1407.6).

Example 2

Synthesis of disulphide [Cys$^{2-6}$] thioether cyclo [CH$_2$CO-Lys(cPn216-glutaryl)-Cys$^2$-Arg-Gly-Asp-Cys$^6$-Phe-Cys]-(PEG)n-NH$_2$ where n=1. (SEQ ID NO. 1)

2 a) Synthesis of 17-(Fmoc-amino)-5-oxo-6-aza-3,9,12,15-tetraoxaheptadecanoic acid This building block is coupled to the solid-phase using Fmoc chemistry. The coupled form of this building block will be referred to in short as (PEG)$_n$ where n is a positive integer.

1,11-Diazido-3,6,9-trioxaundecane

A solution of dry tetraethylene glycol (19.4 g, 0.100 mol) and methanesulphonyl chloride (25.2 g, 0.220 mol) in dry THF (100 ml) was kept under argon and cooled to 0° C. in an ice/water bath. To the flask was added a solution of triethylamine (22.6 g, 0.220 mol) in dry THF (25 ml) dropwise over 45 min. After 1 hr the cooling bath was removed and stirring was continued for 4 hrs. Water (60 ml) was added. To the mixture was added sodium hydrogencarbonate (6 g, to pH 8) and sodium azide (14.3 g, 0.220 mmol), in that order. THF was removed by distillation and the aqueous solution was refluxed for 24 h (two layers formed). The mixture was cooled and ether (100 ml) was added. The aqueous phase was saturated with sodium chloride. The phases were separated and the aqueous phase was extracted with ether (4×50 ml). Combined organic phases were washed with brine (2×50 ml) and dried (MgSO$_4$). Filtration and concentration gave 22.1 g (91%) of yellow oil. The product was used in the next step without further purification.

11-Azido-3,6,9-trioxaundecanamine

To a mechanically, vigorously stirred suspension of 1,11-diazido-3,6,9-trioxaundecane (20.8 g, 0.085 mol) in 5% hydrochloric acid (200 ml) was added a solution of triphenylphosphine (19.9 g, 0.073 mol) in ether (150 ml) over 3 hrs

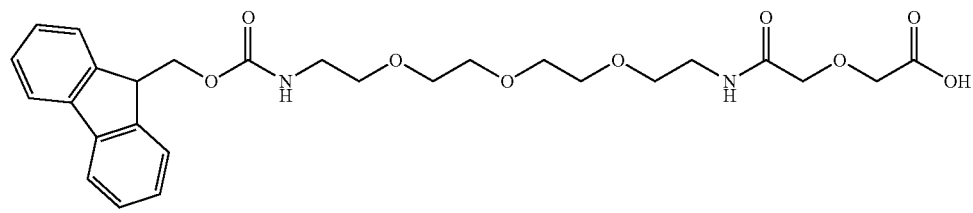

at room temperature. The reaction mixture was stirred for additional 24 hrs. The phases were separated and the aqueous phase was extracted with dichloromethane (3×40 ml). The aqueous phase was cooled in an ice/water bath and pH was adjusted to ca 12 by addition of KOH. The product was extracted into dichloromethane (5×50 ml). Combined organic phases were dried (MgSO$_4$). Filtration and evaporation gave 14.0 g (88%) of yellow oil. Analysis by MALDI-TOF mass spectroscopy (matrix: α-cyano-4-hydroxycinnamic acid) gave a M+H peak at 219 as expected. Further characterisation using $^1$H (500 MHz) and $^{13}$C (125 MHz) NMR spectroscopy verified the structure.

17-Azido-5-oxo-6-aza-3,9,12,15-tetraoxaheptadecanoic acid

To a solution of 11-azido-3,6,9-trioxaundecanamine (10.9 g, 50.0 mmol) in dichloromethane (100 ml) was added diglycolic anhydride (6.38 g, 55.0 mmol). The reaction mixture was stirred overnight. HPLC analysis (column Vydac 218TP54; solvents: A=water/0.1% TFA and B=acetonitrile/0.1% TFA; gradient 4-16% B over 20 min; flow 1.0 ml/min; UV detection at 214 and 284 nm), showed complete conversion of starting material to a product with retention time 18.3 min. The solution was concentrated to give quantitative yield of a yellow syrup. The product was analysed by LC-MS (ES ionisation) giving [MH]+ at 335 as expected. $^1$H (500 MHz) and $^{13}$C (125 MHz) NMR spectroscopy was in agreement with structure The product was used in the next step without further purification.

17-Amino-5-oxo-6-aza-3,9,12,15-tetraoxaheptadecanoic acid

A solution of 17-azido-5-oxo-6-aza-3,9,12,15-tetraoxaheptadecanoic acid (8.36 g, 25.0 mmol) in water (100 ml) was reduced using H$_2$(g)-Pd/C (10%). The reaction was run until LC-MS analysis showed complete conversion of starting material (column Vydac 218TP54; solvents: A=water/0.1% TFA and B=acetonitrile/0.1% TFA; gradient 4-16% B over 20 min; flow 1.0 ml/min; UV detection at 214 and 284 nm, ES ionisation giving M+H at 335 for starting material and 309 for the product). The solution was filtered and used directly in the next step.

17-(Fmoc-amino)-5-oxo-6-aza-3,9,12,15-tetraoxaheptadecanoic acid

To the aqueous solution of 17-amino-5-oxo-6-aza-3,9,12,15-tetraoxaheptadecanoic acid from above (corresponding to 25.0 mmol amino acid) was added sodium bicarbonate (5.04 g, 60.0 mmol) and dioxan (40 ml). A solution of Fmoc-chloride (7.11 g, 0.275 mol) in dioxan (40 ml) was added dropwise. The reaction mixture was stirred overnight. Dioxan was evaporated off (rotavapor) and the aqueous phase was extracted with ethyl acetate. The aqueous phase was acidified by addition of hydrochloric acid and precipitated material was extracted into chloroform. The organic phase was dried (MgSO$_4$), filtered and concentrated to give 11.3 g (85%) of a yellow syrup. The structure was confirmed by LC-MS analysis (column Vydac 218TP54; solvents: A=water/0.1% TFA and B=acetonitrile/0.1% TFA; gradient 40-60% B over 20 min; flow 1.0 ml/min; UV detection at 214 and 254 nm, ES ionisation giving M+H at 531 as expected for the product peak at 5.8 minutes). The analysis showed very low content of side products and the material was used without further purification.

2 b) Synthesis of ClCH$_2$CO-Lys-Cys(tBu)-Arg-Gly-Asp-Cys(tBu)-Phe-Cys-(PEG)n-NH$_2$ where n=1 (SEQ ID NO. 1)

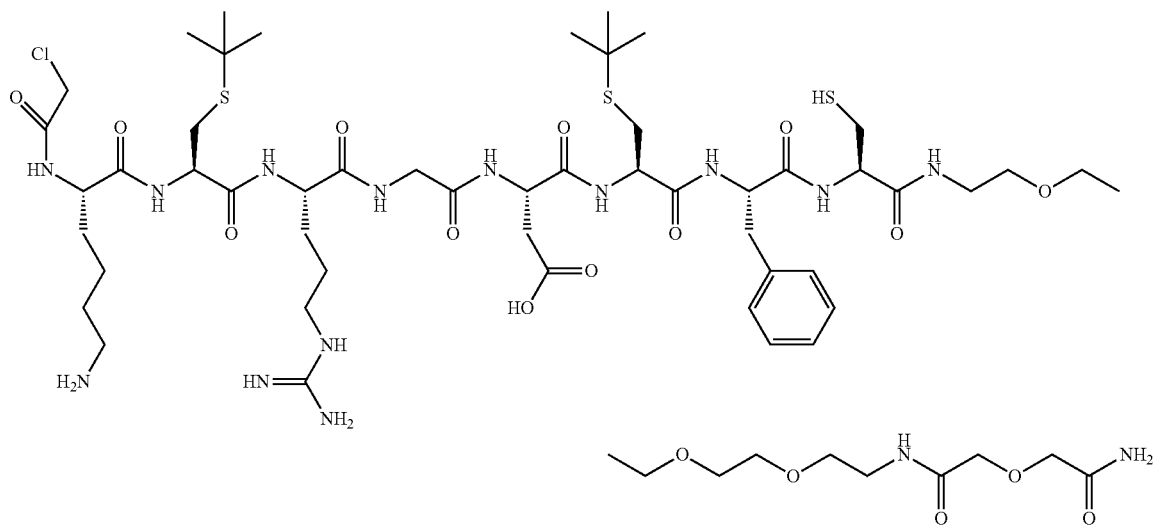

Molecular Weight = 1409.163
Exact Mass = 1407.612
Molecular Formula = C58H98ClN15O17S3

The PEG unit was coupled manually to Rink Amide AM resin, starting on a 0.25 mmol scale, mediated by HATU activation. The remaining peptide was assembled on an ABI 433A automatic peptide synthesiser using 1 mmol amino acid cartridges. The amino acids were pre-activated using HBTU before coupling. N-terminal amine groups were chloroacetylated using a solution of chloroacetic anhydride in DMF for 30 min.

The simultaneous removal of peptide and side-chain protecting groups (except tBu) from the resin was carried out in TFA containing TIS (5%), H$_2$0 (5%) and phenol (2.5%) for two hours.

After work-up 322 mg of crude peptide was obtained (Analytical HPLC: Gradient, 5-50% B over 10 min where A=H$_2$O/ 0.1% TFA and B=CH$_3$CN/0.1% TFA; column, Phenomenex Luna 3μ C18 (2) 50×4.6 mm; flow, 2 mL/min; detection, UV 214 nm; product retention time, 6.37 min). Further product characterisation was carried out using mass spectrometry: Expected, M+H at 1409, found, at 1415).

2 c) Synthesis of thioether cyclo[CH$_2$CO-Lys-Cys(tBu)-Arg-Gly-Asp-Cys(tBu)-Phe-Cys]-(PEG)n-NH$_2$ where n=1 (SEQ ID NO. 1)

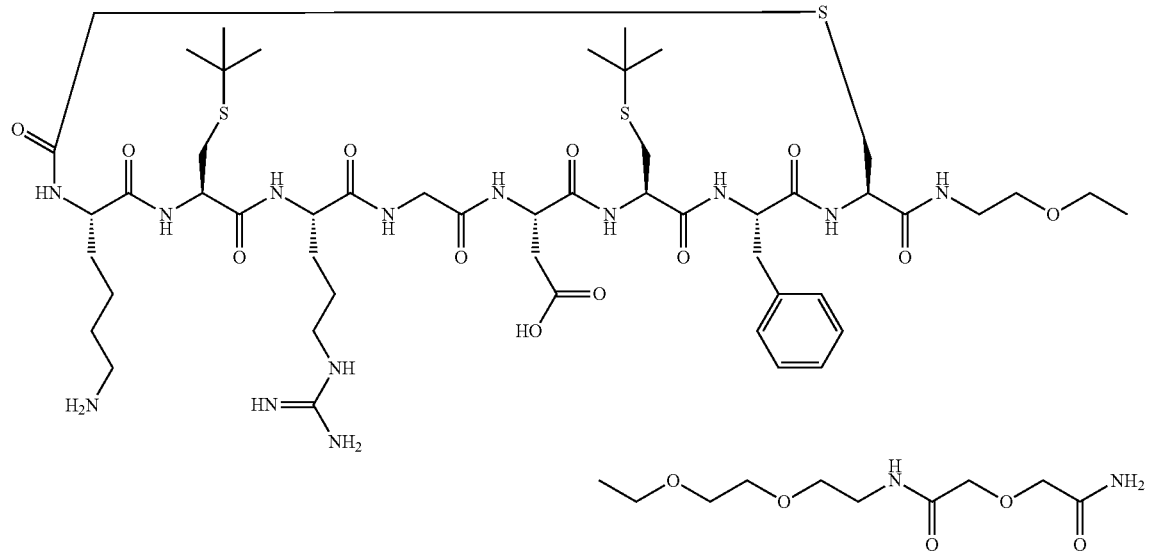

Molecular Weight = 1372.702
Exact Mass = 1371.635
Molecular Formula = C58H97N15O17S3

322 mg of ClCH$_2$CO-Lys-Cys(tBu)-Arg-Gly-Asp-Cys(tBu)-Phe-Cys-(PEG)n-NH$_2$ (SEQ ID NO. 1) was dissolved in water/acetonitrile. The mixture was adjusted to pH 8 with ammonia solution and stirred for 16 hours.

After work-up crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 6.22 min). Further product characterisation was carried out using mass spectrometry: Expected, M+H at 1373, found, at 1378).

2 d) Synthesis of disulphide [Cys$^{2-6}$] thioether cyclo[CH$_2$CO-Lys-Cys$^2$-Arg-Gly-Asp-Cys$^6$-Phe-Cys]-(PEG)n-NH$_2$ where n=1 (SEQ ID NO. 1)

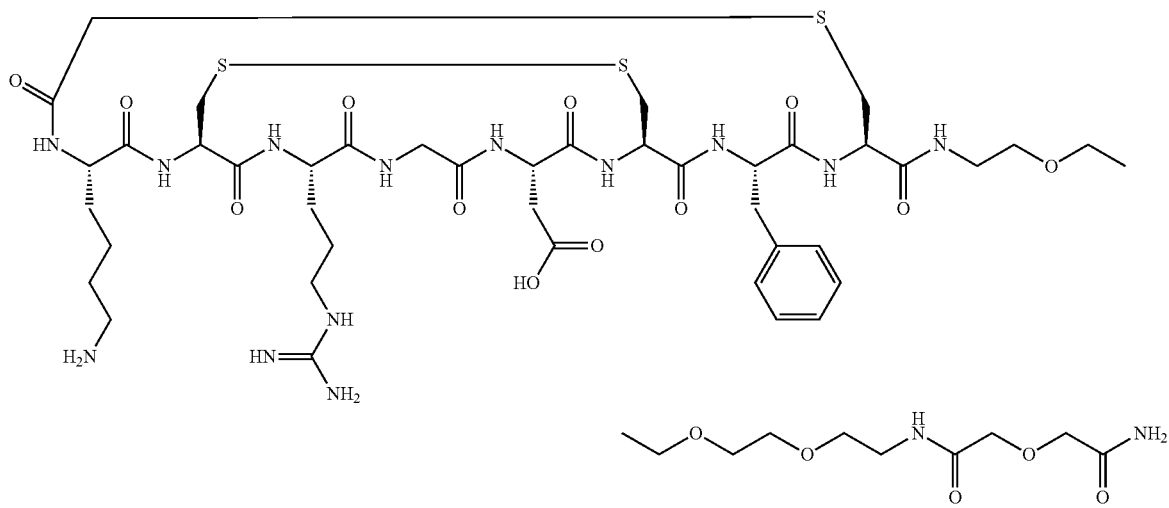

Molecular Weight = 1258.469
Exact Mass = 1257.494
Molecular Formula = C50H79N15O17S3

Thioether cyclo[CH$_2$CO-Lys-Cys(tBu)-Arg-Gly-Asp-Cys(tBu)-Phe-Cys]-(PEG)n-NH$_2$ (SEQ ID NO. 1) was treated with a solution of anisole (200 µL), DMSO (2 mL) and TFA (100 mL) for 60 min following which the TFA was removed in vacuo and the peptide precipitated by the addition of diethyl ether.

Purification by preparative HPLC (Phenomenex Luna 5µ C18 (2) 250×21.20 mm column) of 70 mg crude material was carried out using 0-30% B, where A=H$_2$O/0.1% TFA and B=CH$_3$CN/0.1% TFA, over 40 min at a flow rate of 10 mL/min. After lyophilisation 46 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 6.80 min). Further product characterisation was carried out using mass spectrometry: Expected, M+H at 1258.5, found, at 1258.8).

2 e) Synthesis of disulfide [Cys$^{2-6}$] thioether cyclo[CH$_2$CO-Lys(cPn216-glutaryl)-Cys$^2$-Arg-Gly-Asp-Cys$^6$-Phe-Cys]-(PEG)n-NH$_2$ where n=1 (SEQ ID NO. 1)

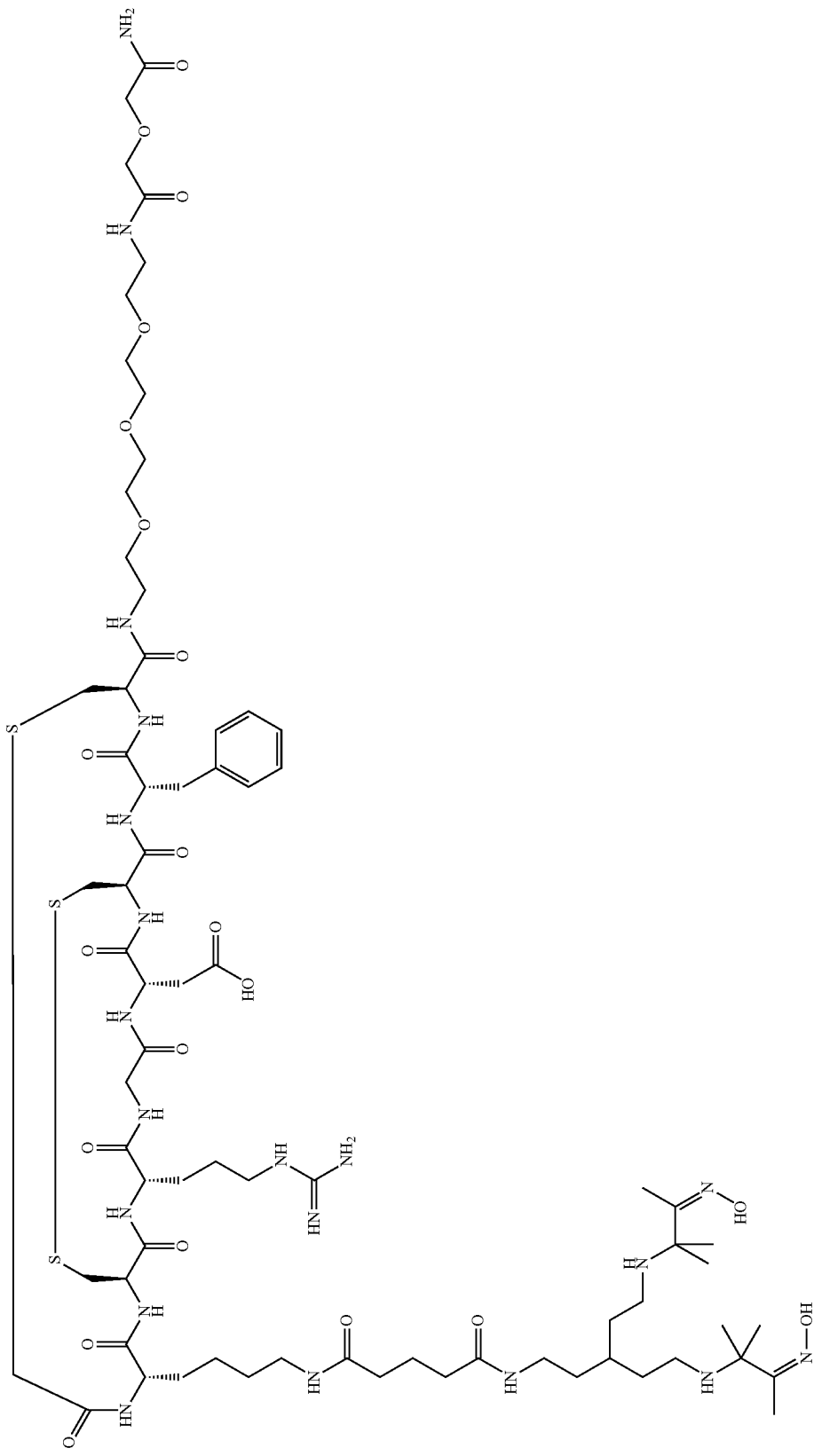

13 mg of [$Cys^{2-6}$] cyclo[$CH_2$CO-Lys-Cys-Arg-Gly-Asp-Cys-Phe-Cys]-(PEG)n-$NH_2$, (SEQ ID NO. 1) 9.6 mg of cPn216 chelate active ester and 8 μL of N-methylmorpholine was dissolved in DMF (0.5 mL). The mixture was stirred for 2 hours and 30 minutes.

Purification by preparative HPLC (Phenomenex Luna 5μ C18 (2) 250×21.20 mm column) of the reaction mixture was carried out using 0-30% B, where A=$H_2O$/0.1% TFA and B=$CH_3CN$/0.1% TFA, over 40 min at a flow rate of 10 mL/min. After lyophilisation 14.2 mg of pure material was obtained (Analytical HPLC: Gradient, 0-30% B over 10 min where A=$H_2O$/0.1% TFA and B=$CH_3CN$/0.1% TFA; column, Phenomenex Luna 3μ C18 (2) 50×4.6 mm; flow, 2 mL/min; detection, UV 214 nm; product retention time, 7.87 min). Further product characterisation was carried out using mass spectrometry: Expected, M+H at 1697.8, found, at 1697.9).

Example 3

Synthesis of disulfide [$Cys^{2-6}$] thioether cyclo [$CH_2$CO-Lys(cPn216-glutaryl)-$Cys^2$-Arg-Gly-Asp-$Cys^6$-Phe-Cys]-(PEG)n-$NH_2$ where n=2. (SEQ ID NO. 1)

3 a) Synthesis of $ClCH_2$CO-Lys-Cys(tBu)-Arg-Gly-Asp-Cys(tBu)-Phe-Cys-(PEG)n-$NH_2$ where n=2 (SEQ ID NO. 1)

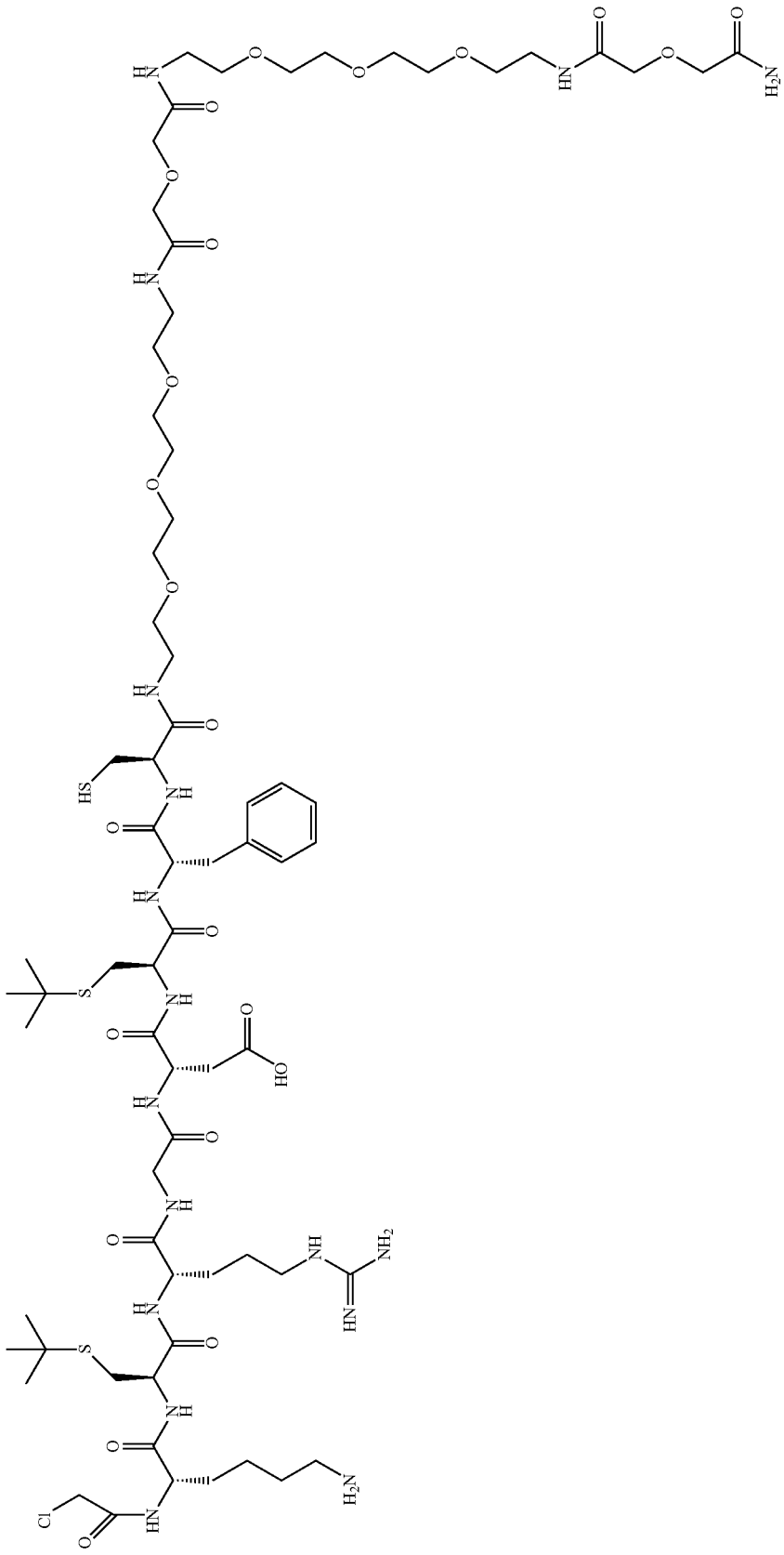
Molecular Weight = 1699.482
Exact Mass = 1697.759
Molecular Formula = C70H120ClN17O23S3

Assembly of peptide as for example 2 b), both PEG units coupled manually.

After work-up crude peptide was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 mL/min; detection, UV 214 nm; product retention time, 6.40 min).

3 b) Synthesis of thioether cyclo[$CH_2$CO-Lys-Cys(tBu)-Arg-Gly-Asp-Cys(tBu)-Phe-Cys]-(PEG)n-$NH_2$ where n=2 (SEQ ID NO. 1)

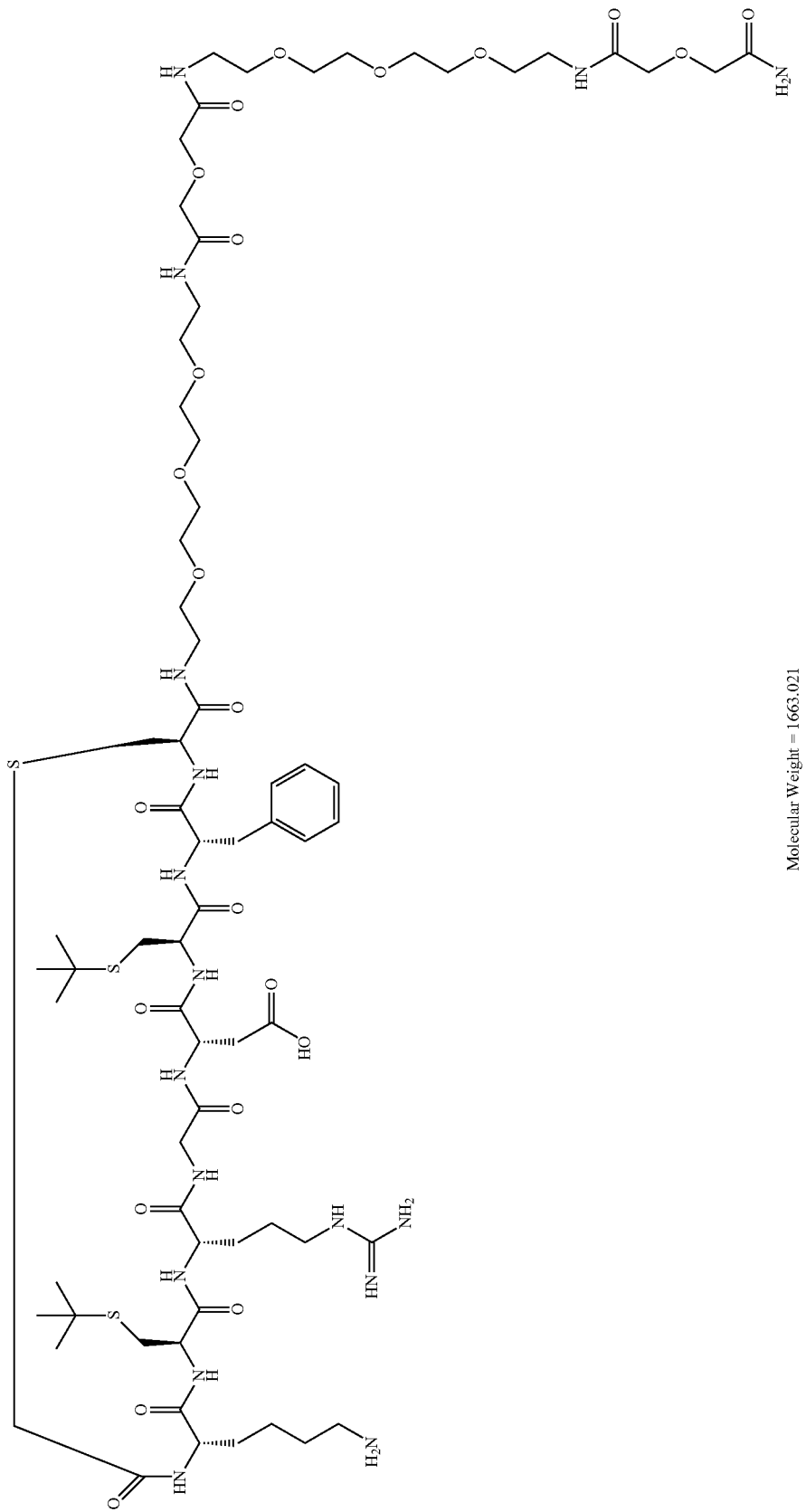

ClCH$_2$CO-Lys-Cys(tBu)-Arg-Gly-Asp-Cys(tBu)-Phe-Cys-(PEG)n-NH$_2$ (SEQ ID NO. 1) where n=2 was dissolved in water/acetonitrile. The mixture was adjusted to pH 8 with ammonia solution and stirred for 16 hours.

After work-up 380 mg of crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 6.28 min). Further product characterisation was carried out using mass spectrometry: Expected, M+H at 1663, found, at 1670).

3 c) Synthesis of disulphide [Cys$^{2-6}$] thioether cyclo[CH$_2$CO-Lys-Cys$^2$-Arg-Gly-Asp-Cys$^6$-Phe-Cys]-(PEG)n-NH$_2$ where n=2. (SEQ ID NO. 1)

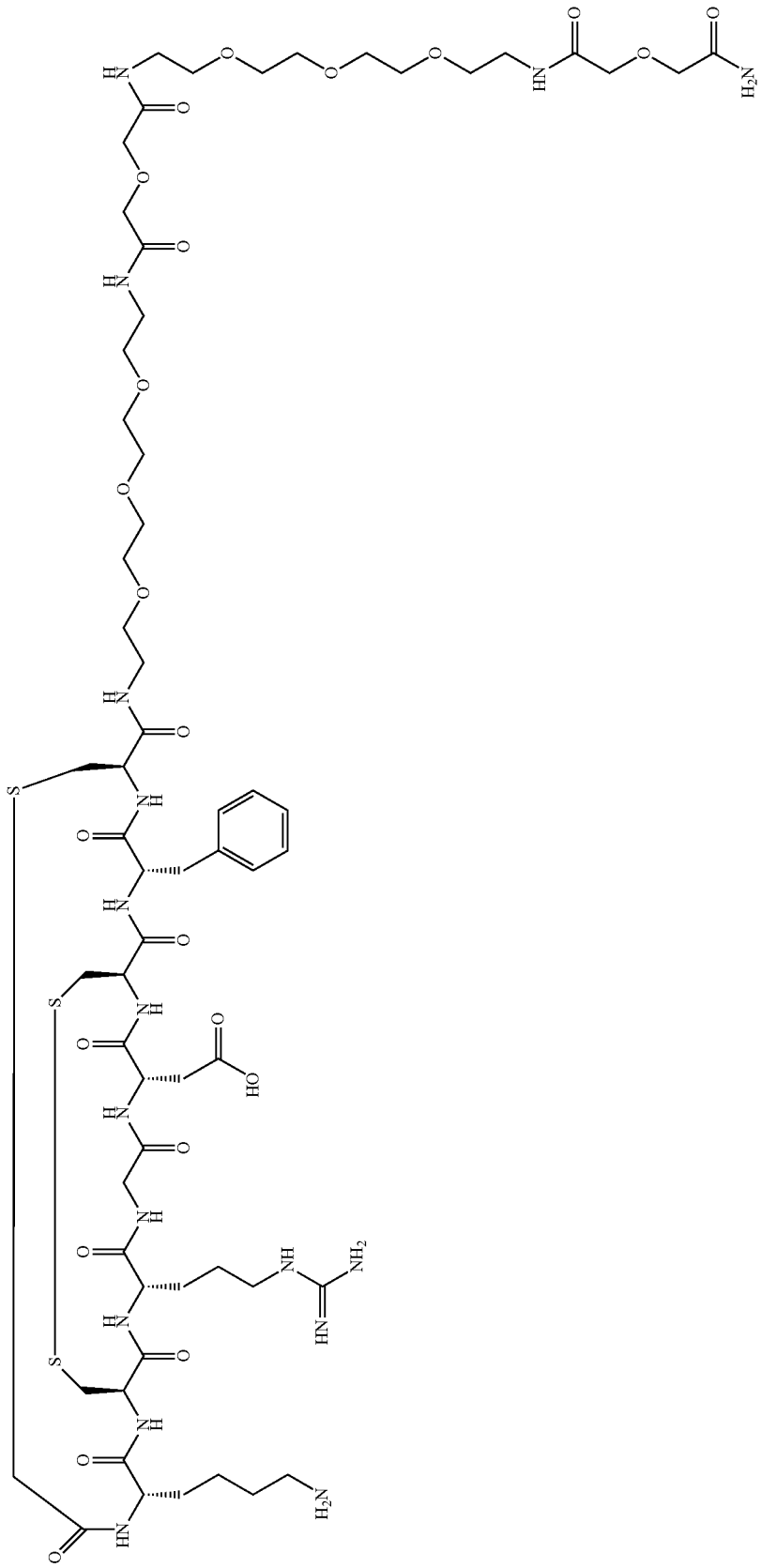

380 mg of thioether cyclo[CH$_2$CO-Lys-Cys(tBu)-Arg-Gly-Asp-Cys(tBu)-Phe-Cys]-(PEG)n-NH$_2$ where n=2 (SEQ ID NO. 1) was treated with a solution of anisole (500 μL), DMSO (2 mL) and TFA (100 mL) for 60 min following which the TFA was removed in vacuo and the peptide precipitated by the addition of diethyl ether.

Purification by preparative HPLC (Phenomenex Luna 10μ C18 (2) 250×50 mm column) of the crude material (345 mg) was carried out using 0-30% B, where A=H$_2$O/0.1% TFA and B=CH$_3$CN/0.1% TFA, over 60 min at a flow rate of 50 mL/min. After lyophilisation 146 mg of pure material was obtained (Analytical HPLC: Gradient, 0-30% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 7.42 min). Further product characterisation was carried out using mass spectrometry: Expected, M+H at 1548.6, found, at 1548.8).

3 d) Synthesis of disulphide [Cys$^{2-6}$] thioether cyclo [CH$_2$CO-Lys(cPn216-glutaryl)-Cys$^2$-Arg-Gly-Asp-Cys$^6$-Phe-Cys]-(PEG)n-NH$_2$ where n=2. (SEQ ID NO. 1)

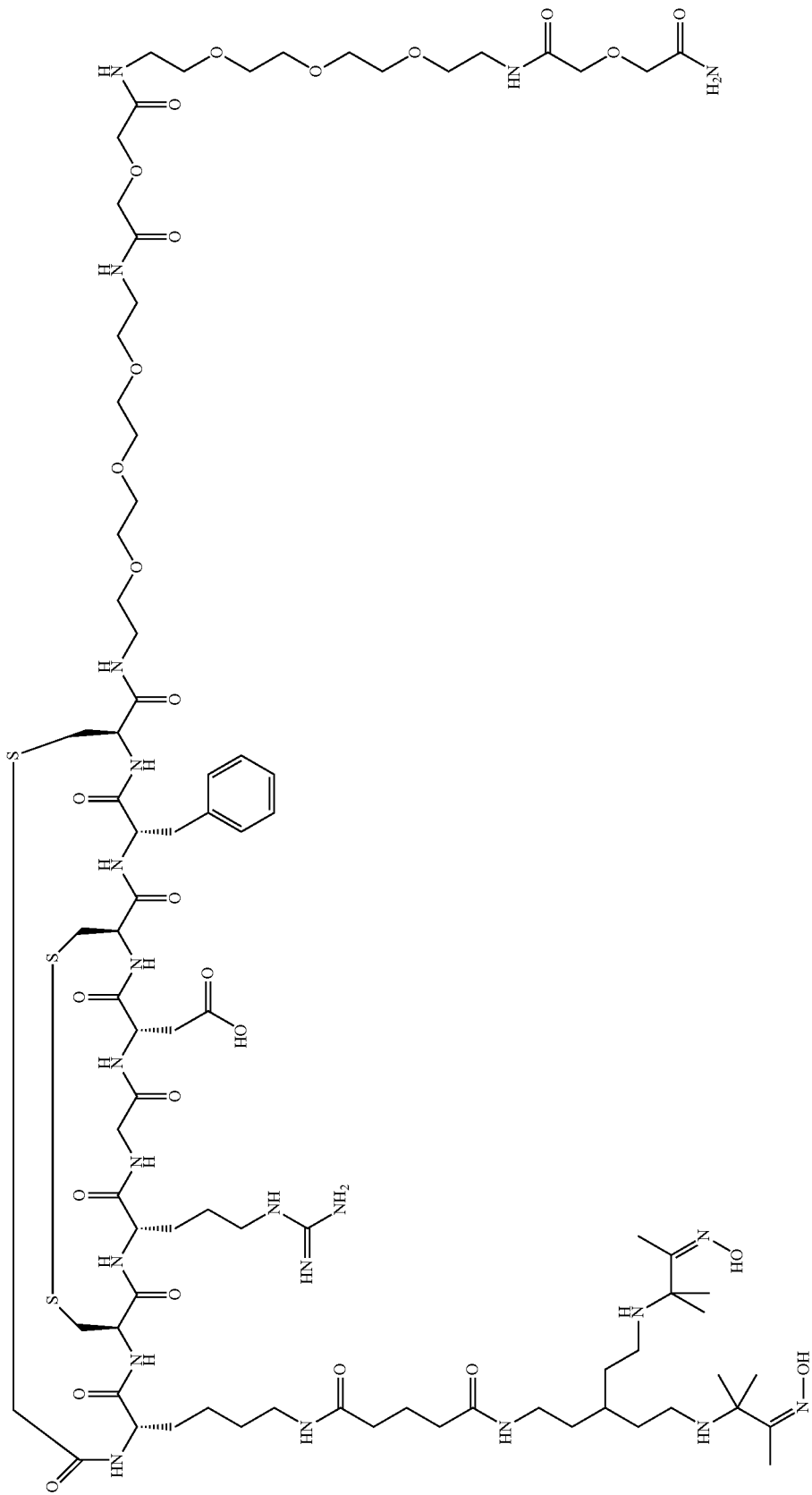

146 mg of [Cys$^{2-6}$] cyclo[CH$_2$CO-Lys-Cys-Arg-Gly-Asp-Cys-Phe-Cys]-(PEG)$_2$-NH$_2$, (SEQ ID NO. 1) 110 mg of cPn216 chelate active ester and 76 µL of N-methylmorpholine was dissolved in DMF (6 mL). The mixture was stirred for 9 hours.

Purification by preparative HPLC (Phenomenex Luna 10µ C18 (2) 250×50 mm column) of the reaction mixture was carried out using 0-30% B, where A=H$_2$O/0.1% TFA and B=CH$_3$CN/0.1% TFA, over 60 min at a flow rate of 50 mL/min. After lyophilisation 164 mg of pure material was obtained (Analytical HPLC: Gradient, 0-30% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 8.13 min). Further product characterisation was carried out using mass spectrometry: Expected, M+H at 1988.0, found, at 1988.0).

Example 4

Synthesis of disulfide [Cys$^{2-6}$] thioether cyclo [CH$_2$CO-Lys(cPn216-glutaryl)-Cys$^2$-Arg-Gly-Asp-Cys$^6$-Phe-Cys]-(PEG)n-NH$_2$ where n=4. (SEQ ID NO. 1)

4 a) Synthesis of ClCH$_2$CO-Lys-Cys(tBu)-Arg-Gly-Asp-Cys(tBu)-Phe-Cys-(PEG)n-NH$_2$ where n=4 (SEQ ID NO. 1)

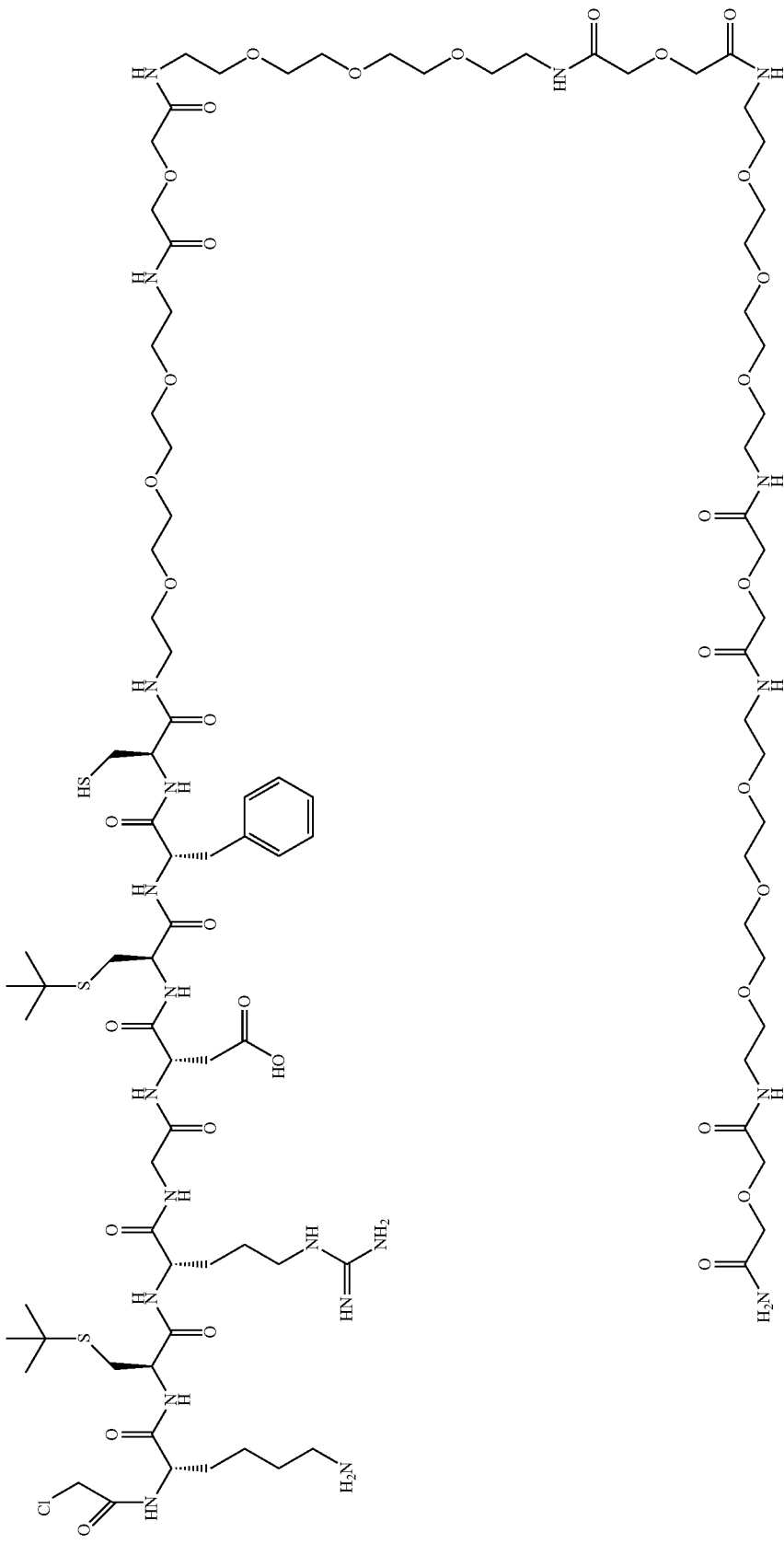

Assembly of peptide as for example 2 b), all four PEG units coupled manually.

After work-up crude peptide was obtained (Analytical HPLC: Gradient, 5-50% B over 10 min where A=H₂O/0.1% TFA and B=CH₃CN/0.1% TFA; column, Phenomenex Luna 3μ C18 (2) 50×4.6 mm; flow, 2 mL/min; detection, UV 214 nm; product retention time, 6.50 min).

4 b) Synthesis of thioether cyclo[CH₂CO-Lys-Cys(tBu)-Arg-Gly-Asp-Cys(tBu)-Phe-Cys]-(PEG)n-NH₂ where n=4 (SEQ ID NO. 1)

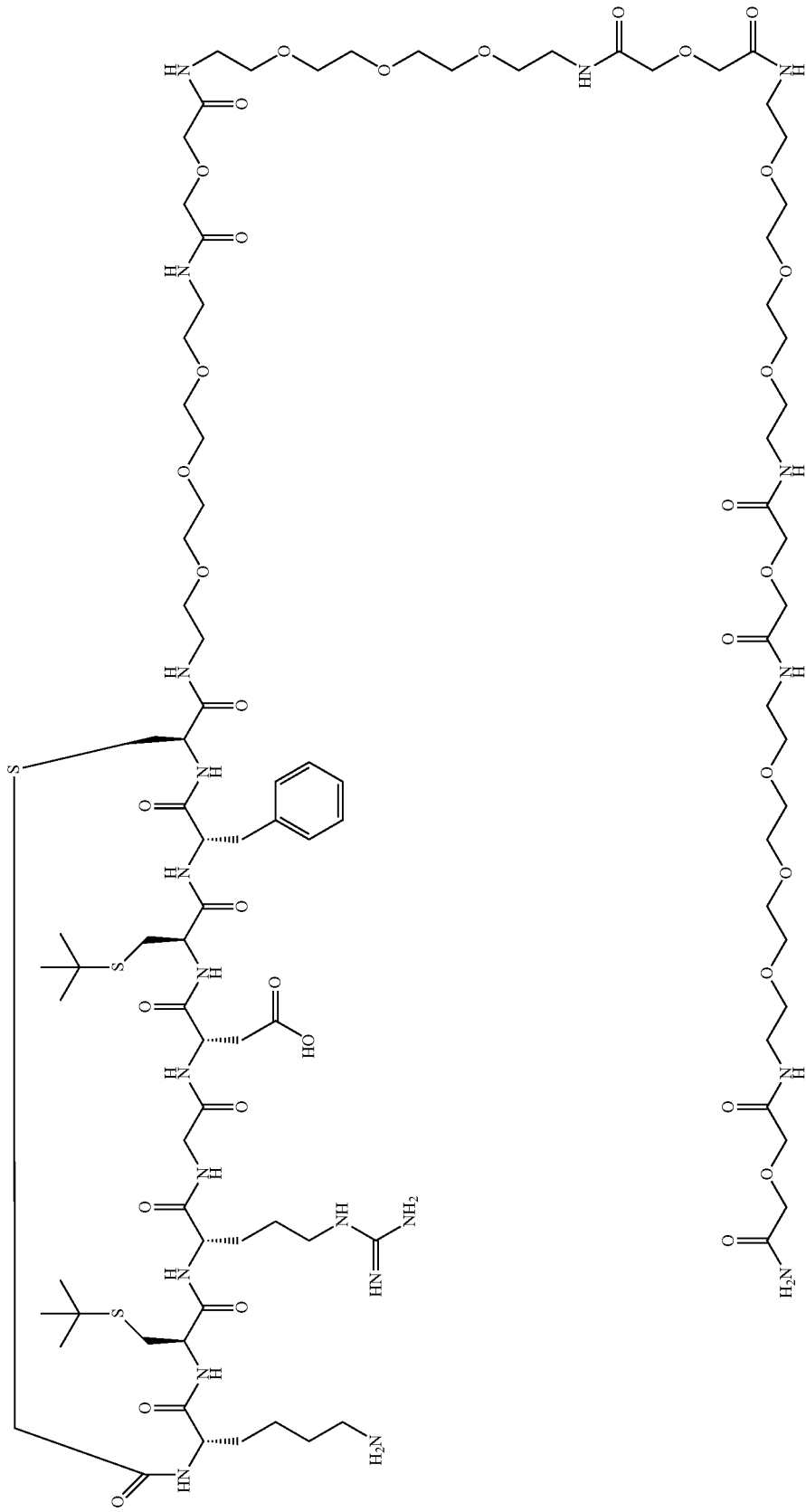

ClCH$_2$CO-Lys-Cys(tBu)-Arg-Gly-Asp-Cys(tBu)-Phe-Cys-(PEG)$_4$-NH$_2$ (SEQ ID NO. 1) was dissolved in water/acetonitrile. The mixture was adjusted to pH 8 with ammonia solution and stirred for 16 hours.

After work-up crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 6.37 min). Further product characterisation was carried out using mass spectrometry: Expected, [(M+2H)/2] at 1122.0, found, at 1122.5).

4 c) Synthesis of disulphide [Cys$^{2-6}$] thioether cyclo[CH$_2$CO-Lys-Cys$^2$-Arg-Gly-Asp-Cys$^6$-Phe-Cys]-(PEG)n-NH$_2$ where n=4 (SEQ ID NO. 1)

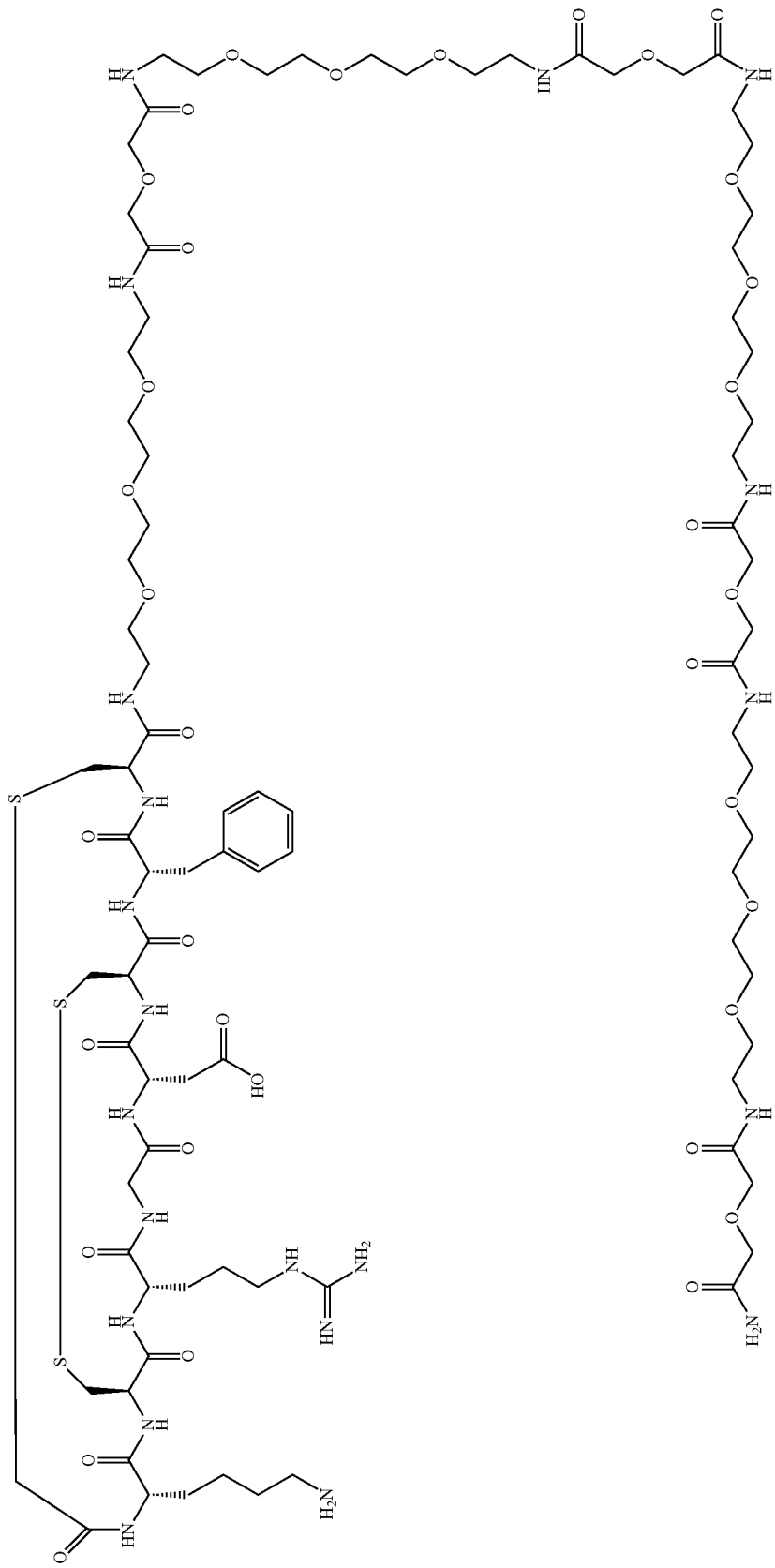

Thioether cyclo[CH$_2$CO-Lys-Cys(tBu)-Arg-Gly-Asp-Cys(tBu)-Phe-Cys]-(PEG)$_4$-NH$_2$ (SEQ ID NO. 1) was treated with a solution of anisole (100 µL), DMSO (1 mL) and TFA (50 mL) for 60 min following which the TFA was removed in vacuo and the peptide precipitated by the addition of diethyl ether.

Purification by preparative HPLC (Phenomenex Luna 5µ C18 (2) 250×21.20 mm column) of the crude material (345 mg) was carried out using 5-50% B, where A=H$_2$O/0.1% TFA and B=CH$_3$CN/0.1% TFA, over 40 min at a flow rate of 10 mL/min. After lyophilisation 12 mg of pure material was obtained (Analytical HPLC: Gradient, 5-50% B over 10 min where A=H$_2$O/0.1% TFA and B=CH$_3$CN/0.1% TFA; column, Phenomenex Luna 3µ C18 (2) 50×4.6 mm; flow, 2 mL/min; detection, UV 214 nm; product retention time, 4.87 min).

4 d) Synthesis of disulphide [Cys$^{2-6}$] thioether cyclo [CH$_2$CO-Lys(cPn216-glutaryl)-Cys$^2$-Arg-Gly-Asp-Cys$^6$-Phe-Cys]-(PEG)n-NH$_2$ where n=4. (SEQ ID NO. 1)

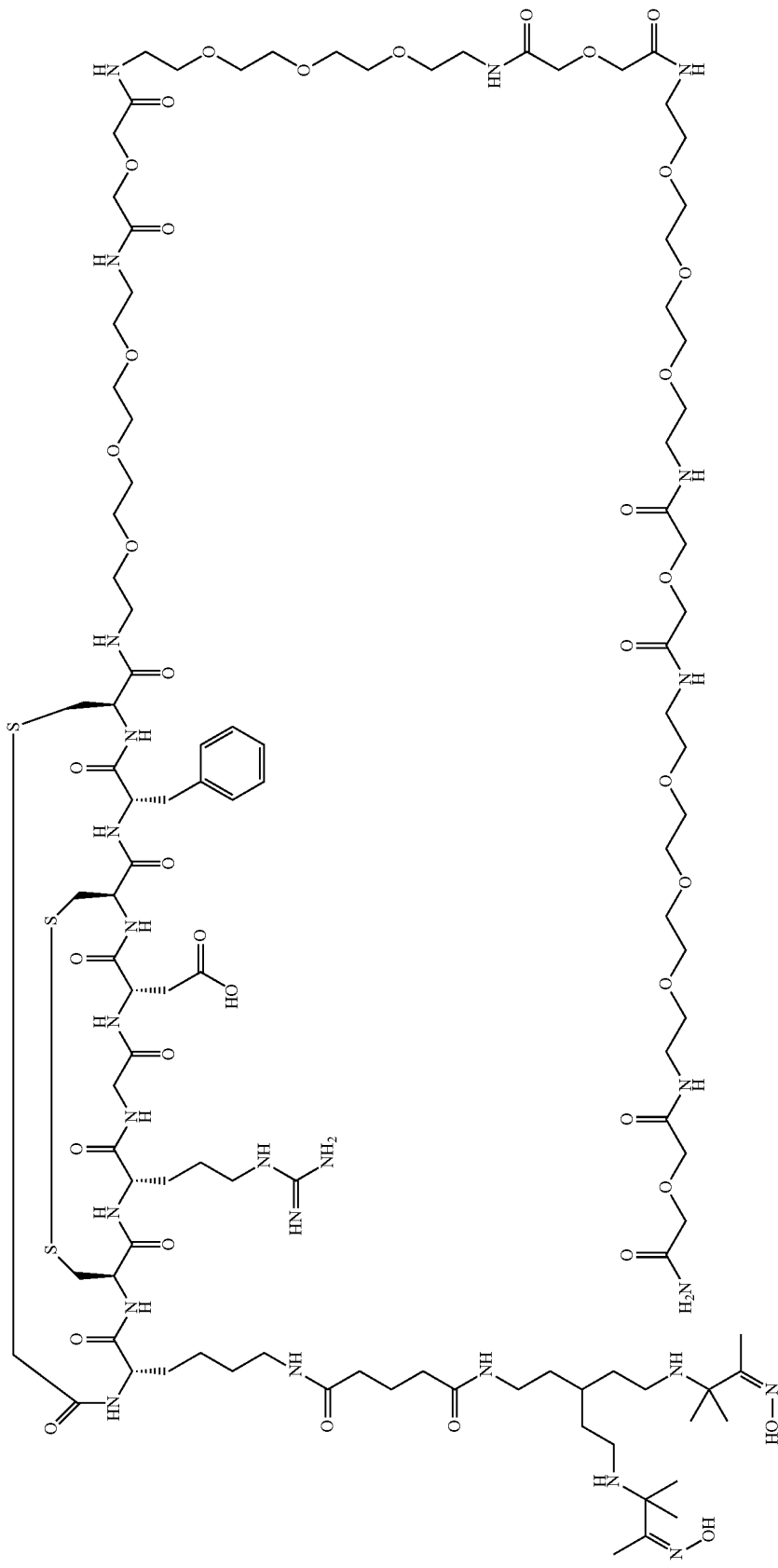

12 mg of disulphide [Cys$^{2-6}$] thioether cyclo[CH$_2$CO-Lys-Cys-Arg-Gly-Asp-Cys-Phe-Cys]-(PEG)$_4$-NH$_2$, (SEQ ID NO. 1) 5.2 mg of cPn216 chelate active ester and 2 μL of N-methylmorpholine was dissolved in DMF (0.5 mL). The mixture was stirred for 7 hours.

Purification by preparative HPLC (Phenomenex Luna 5μ C18 (2) 250×21.20 mm column) of the reaction mixture was carried out using 5-50% B, where A=H$_2$O/0.1% TFA and B=CH$_3$CN/0.1% TFA, over 40 min at a flow rate of 10 mL/min. After lyophilisation 8 mg of pure material was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 mL/min; detection, UV 214 nm; product retention time, 5.17 min). Further product characterisation was carried out using mass spectrometry: Expected, [(M+2H)/2] at 1284.6, found, at 1284.9).

---

---

The invention claimed is:

1. A pharmaceutical composition comprising an effective amount of a compound of formula (I) or a pharmaceutically acceptable salt thereof, together with one or more pharmaceutically acceptable adjuvants, excipients or diluents:

$$\begin{array}{c} Z_1-W_1 \\ | \\ R_1-C(=O)-X_1-X_2-X_3-G-D-X_4-X_5-X_6-X_7 \\ | \qquad\qquad\qquad\qquad\qquad\qquad\qquad | \\ S\text{———————————————}(CH_2)_h \end{array}$$

with S—S bridge between $X_2$ and $X_4$ (I)

wherein:
G represents glycine
D represents aspartic acid
R$_1$ represents —(CH$_2$)$_n$— or —(CH$_2$)$_n$—C$_6$H$_4$— wherein n represents a positive integer 1 to 10
h represents a positive integer 1 or 2
X$_1$ represents an amino acid residue wherein said amino acid possesses a functional side-chain such as an acid or amine,
X$_2$ and X$_4$ represent independently an amino acid residue capable of forming a disulfide bond,
X$_3$ represents arginine, N-methylarginine or an arginine mimetic,
X$_5$ represents a hydrophobic amino acid or derivatives thereof, and
X$_6$ represents a thiol-containing amino acid residue, and
X$_7$ is absent or represents a biomodifier moiety,
Z$_1$ comprises a chelating agent and/or a radionuclide reporter moiety and
W$_1$ is absent or represents a spacer moiety.

2. The composition of claim 1, wherein any of the amino acid residues are independently in the D or L conformation.

3. The composition of claim 1, wherein R$_1$ represents —(CH$_2$)—.

4. The composition of claim 1, wherein X$_1$ represents aspartic acid, glutamic acid, lysine, homolysine or a diaminoalkylic acid or derivatives thereof.

5. The composition of claim 1, wherein X$_2$, X$_4$ and X$_6$ independently represent a cysteine or homocysteine residue.

6. The composition of claim 1, wherein X$_3$ represents an arginine residue.

7. The composition of claim 1, wherein X$_5$ represents a tyrosine, a phenylalanine, a 3-iodo-tyrosine or a naphthylalanine residue.

8. The composition of claim 1, wherein X$_7$ is absent or comprises 1-10 units of a monodisperse PEG building block.

9. The composition of claim 1, wherein X$_7$ is absent or comprises 1-10 units of Formula II $$\left[ H_2N\diagdown\diagup O\diagdown\diagup O\diagdown\diagup O\diagdown\diagup \underset{H}{N}\diagdown\underset{O}{\overset{}{C}}\diagdown\diagup O\diagdown\underset{O}{\overset{}{C}}\diagup \right]_n$$ (II)

10. The composition of claim 1, wherein X$_7$ represent 1-10 amino acid residues.

11. The composition of claim 1, wherein $X_7$ represent glycine, lysine, aspartic acid or serine residues.

12. The composition of claim 1, where $Z_1$ comprises a chelating agent of Formula III

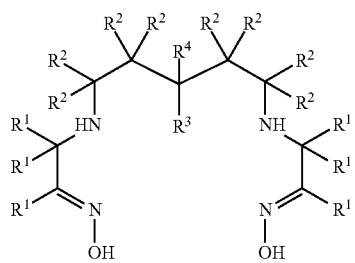

(III)

where:

each $R^1$, $R^2$, $R^3$ and $R^4$ is independently an R group;

each R group is independently H or $C_{1-10}$ alkyl, $C_{3-10}$ alkylaryl, $C_{2-10}$ alkoxyalkyl, $C_{1-10}$ hydroxyalkyl, $C_{1-10}$ alkylamine, $C_{1-10}$ fluoroalkyl, or 2 or more R groups, together with the atoms to which they are attached form a carbocyclic, heterocyclic, saturated or unsaturated ring.

13. The composition of claim 1, where $Z_1$ comprises a chelating agent of formula:

14. The composition of claim 1, wherein $Z_1$ comprises a radionuclide reporter moiety, wherein when said radionuclide is a radiometal, said radiometal is chelated by the chelating agent of $Z_1$.

15. The composition of claim 14, wherein the reporter moiety comprises $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$, $^{141}Ce$ or $^{18}F$.

16. The composition of claim 15, wherein the radionuclide reporter moiety is $^{99m}Tc$.

17. The composition of claim 1, where $W_1$ is glutaric or succinic acid.

18. The composition of claim 1, wherein the compound of Formula (I) is defined by the following formulae:

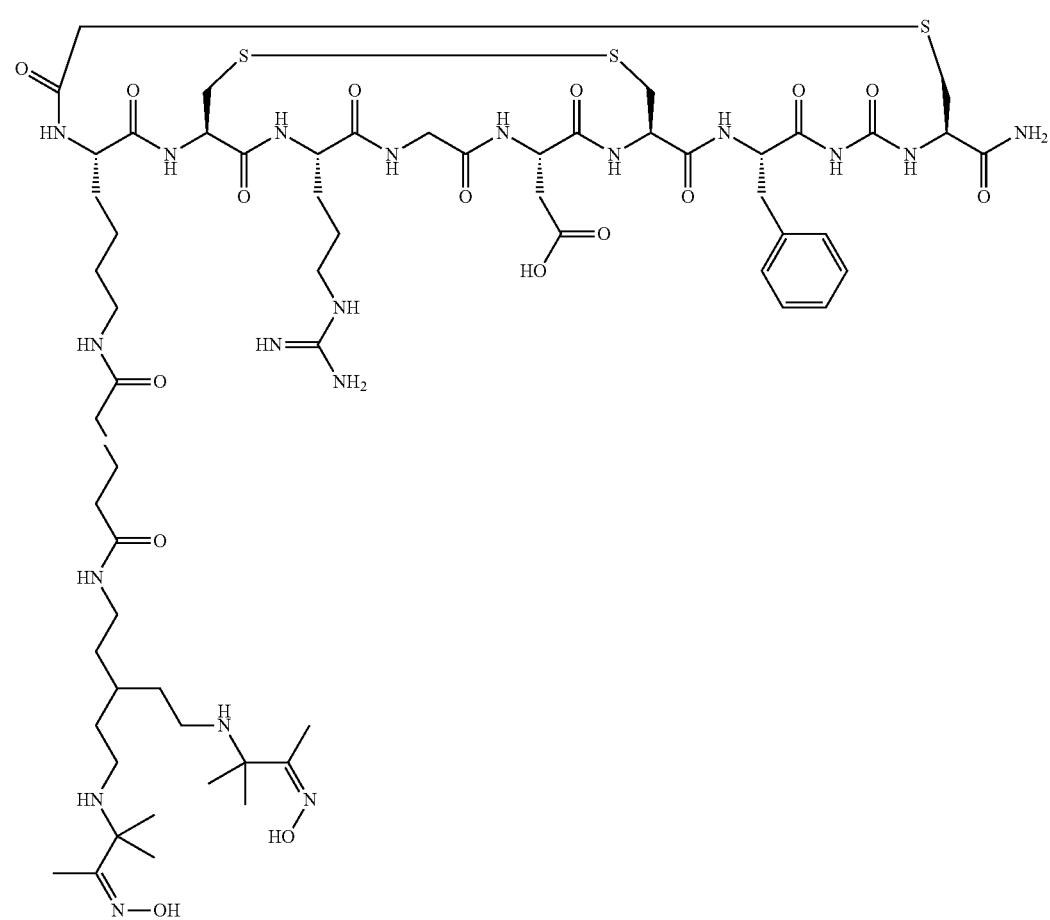

Compound I

-continued
Compound II
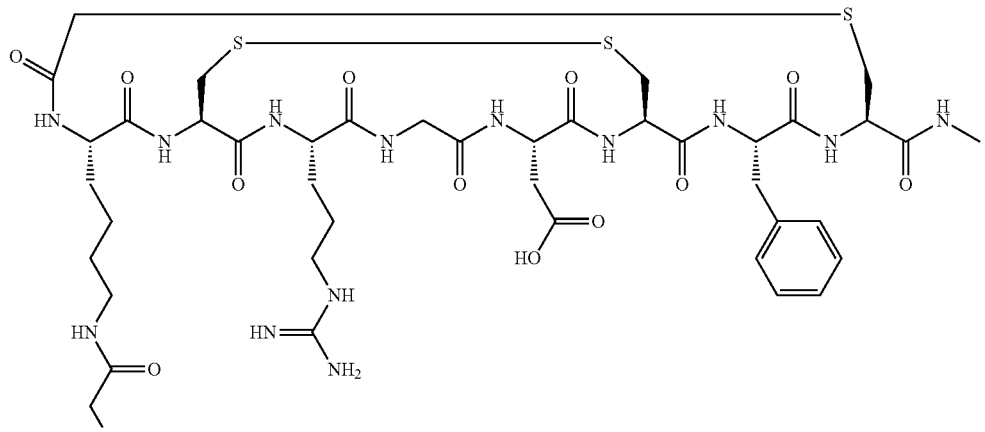
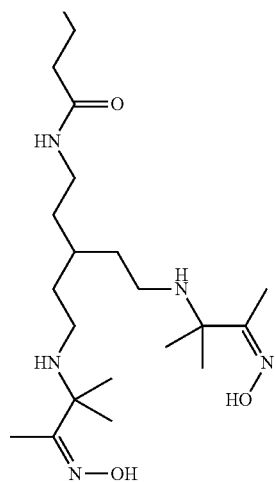
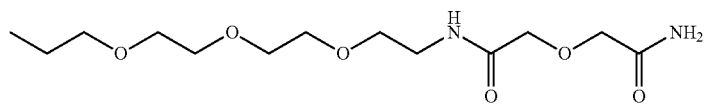
Compound III
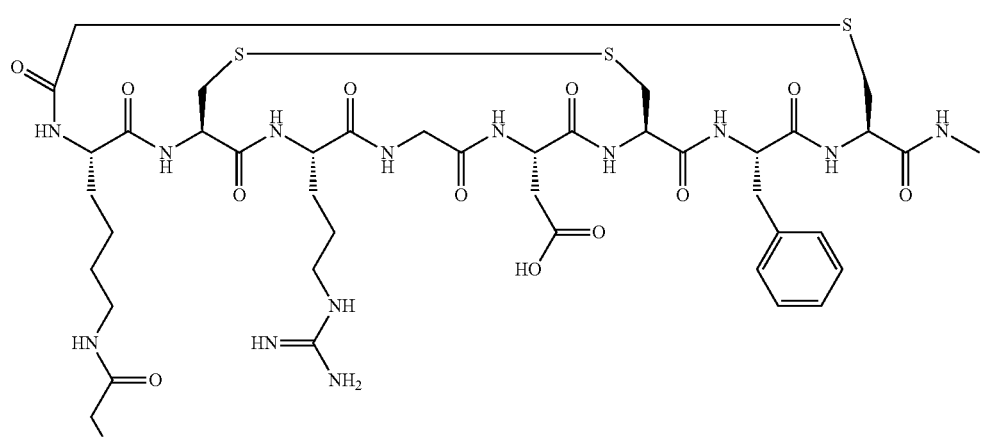

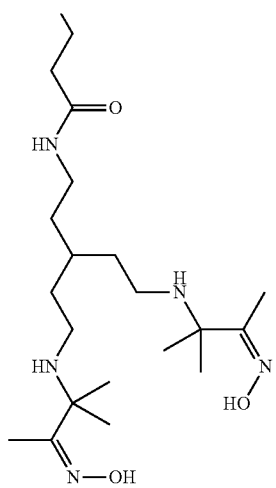
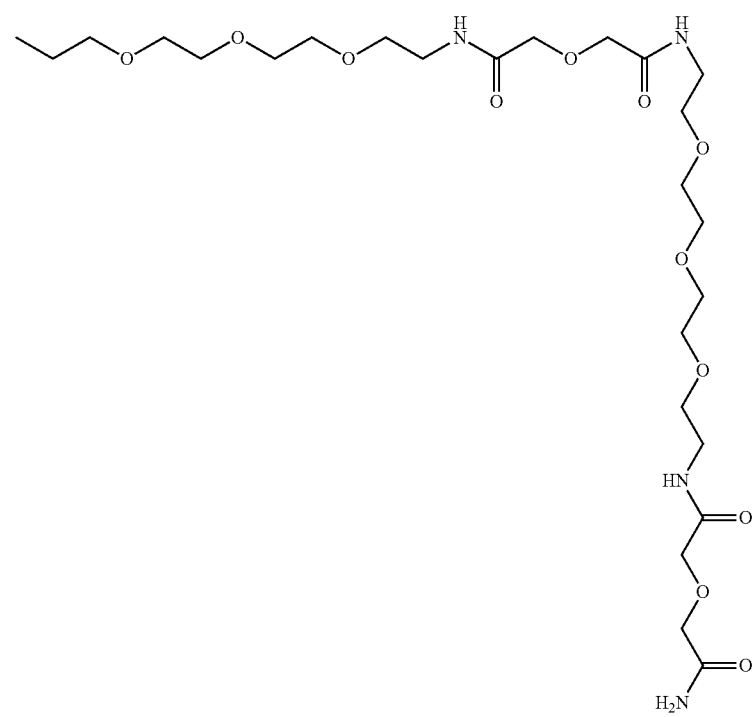
Compound IV
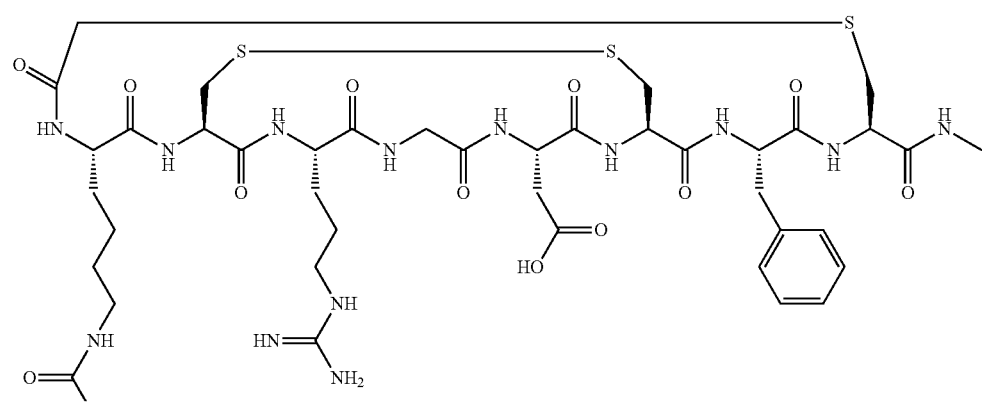

-continued
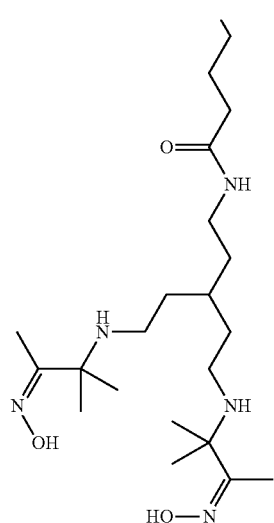
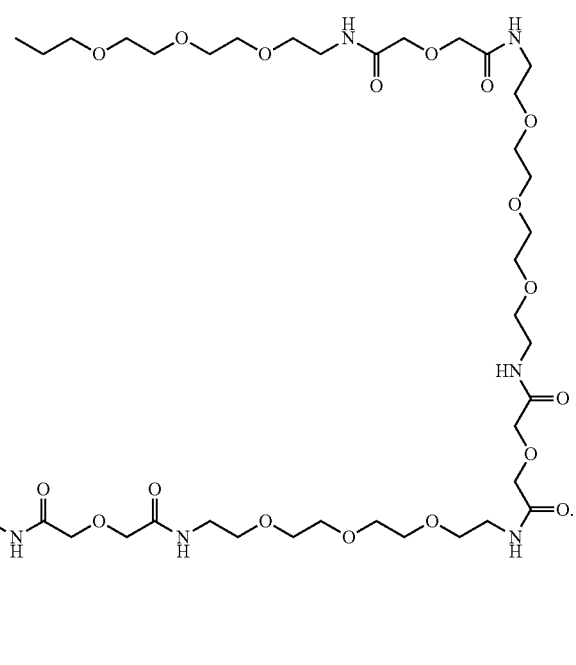
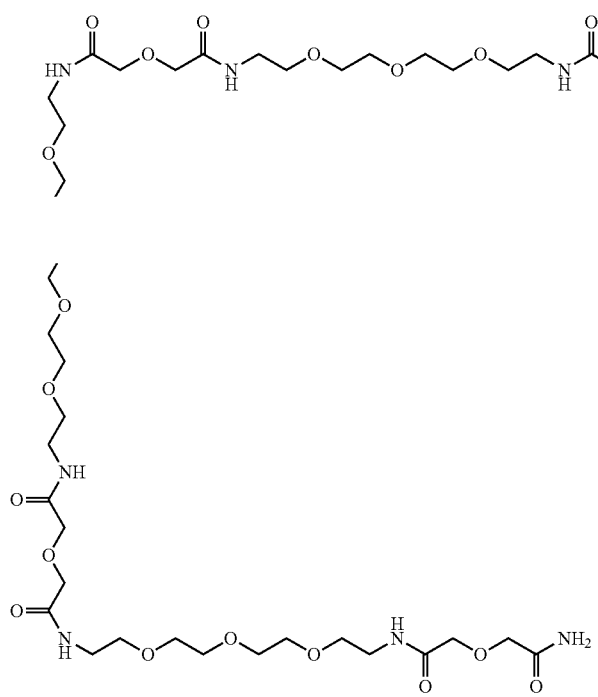

19. A method of generating images of a human or animal body involving administering a contrast agent to said body, and generating an image of at least a part of said body to which said contrast agent has distributed, wherein said contrast agent comprises the composition of claim 14.

20. The method of claim 19, which is carried out to monitor the effect of treatment of a human or animal body with a drug to combat a condition associated with cancer, wherein said administration and image generation are optionally but preferably being effected repeatedly, e.g. before, during and after treatment with said drug.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: THIOETH
<222> LOCATION: (1)..(8)
<223> OTHER INFORMATION: Thioether bridge between amino acid residue 1
      and 8
<220> FEATURE:
<221> NAME/KEY: DISULFID
<222> LOCATION: (2)..(5)
<223> OTHER INFORMATION: Disulphide bridge between amino acid residue 2
      and 5.

<400> SEQUENCE: 1

Lys Cys Arg Gly Asp Cys Phe Cys
1               5